(12) United States Patent
Bittner et al.

(10) Patent No.: US 6,569,626 B2
(45) Date of Patent: *May 27, 2003

(54) METHODS FOR MULTIPLE DIRECT LABEL PROBE DETECTION OF MULTIPLE CHROMOSOMES OR REGIONS THEREOF BY IN SITU HYBRIDIZATION

(75) Inventors: Michael L. Bittner, Naperville, IL (US); Larry E. Morrison, DuPage County, IL (US); Mona S. Legator, Chicago, IL (US)

(73) Assignee: Vysis, Inc., Downers Grove, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/795,953

(22) Filed: Jun. 21, 2001

(65) Prior Publication Data

US 2002/0025523 A1 Feb. 28, 2002

Related U.S. Application Data

(63) Continuation of application No. 09/110,562, filed on Jul. 6, 1998, now Pat. No. 6,277,569, which is a division of application No. 08/781,682, filed on Jan. 10, 1997, now Pat. No. 5,776,688, which is a continuation of application No. 08/476,694, filed on Jun. 7, 1995, now Pat. No. 5,663,319, which is a division of application No. 08/222,167, filed on Apr. 4, 1994, now Pat. No. 5,491,224, which is a continuation of application No. 07/762,913, filed on Sep. 19, 1991, now abandoned, which is a continuation-in-part of application No. 07/585,876, filed on Sep. 20, 1990, now abandoned.

(51) Int. Cl.$^7$ .......................... C12Q 1/68; C07H 21/02; C07H 21/04
(52) U.S. Cl. .......................... 435/6; 536/23.1; 536/24.3
(58) Field of Search ............................ 435/6; 536/23.1, 536/24.3

(56) References Cited

U.S. PATENT DOCUMENTS

| | | | |
|---|---|---|---|
| 4,711,955 A | * 12/1987 | Ward et al. | |
| 4,780,405 A | * 10/1988 | Kaiser et al. | |
| 4,833,251 A | * 5/1989 | Musso et al. | |
| 4,910,300 A | * 3/1990 | Urdea et al. | |
| 5,130,446 A | * 7/1992 | Musso et al. | |
| 5,175,269 A | * 12/1992 | Stavrianopoulos | |
| 5,241,060 A | * 8/1993 | Engelhardt et al. | |
| 5,328,824 A | * 7/1994 | Ward et al. | |
| 5,447,841 A | * 9/1995 | Gray et al. | |
| 5,491,224 A | * 2/1996 | Bittner et al. | |
| 5,776,688 A | * 7/1998 | Bittner et al. | |
| 6,277,569 B1 | * 8/2001 | Bittner et al. | |

OTHER PUBLICATIONS

Trask et al., Detection of DNA Sequences in Nuclei in Suspension by in Situ Hybridization and Dual Beam Flow Cytometry. Science 230 : 1401–1403 (1985).*
Trask et al. Mapping of Human Chromosomes Xq28 by Two–Color Fluorescence In Situ Hybridization of DNA Sequences to Interphase Cell Nuclei. American Journal of Human Genetics. 48 : 1–15 (1991).*
Nederlof et al. Multiple Fluorescence In Situ Hybridization. Cytometry 11:126–131 (1990).*
Nederlof et al. Three–Color Fluorescence In Situ Hybridization for Simultaneous Detection. Cytometry 10 : 20–27 (1988).*
Bresser et al. Comparison and Optimization of In Situ Hybridization Procedures. Gene Anal Techn 4 : 89–104 (1987).*
Haralambidis et al. The Preparation of Polyamide–Oligonucleotide probes containing multiple non–radioactive labels. Nucleic Acids Research 18 (3) : 501–505 (1990).*
Viscidi et al. Novel Chemical Method for the Preparation of Nucleic Acids for Nonisotopic Hybridization. Journal of Clinical Microbiology 23 (2) : 311–317 (Feb. 1986).*
Avignolo et al. Biotinylation of Double Stranded DNA After Transamination. Biochemical and Biophysical Research Communications. 170 (1) : 243–250 (Jul. 1990).*
Hayatsu, H. Reaction of Cytidine with Semicarbazide in the Presence of Bisulfite. A Rapid Modification Specific for Single–Stranded Polynucleotide Biochemistry 15(12) : 2677–2682 (1976).*
Draper et al. A Method for Linking Fluorescent Labels to Polynucleotides: Application to Studies of Ribosome–Ribonucleic Acid Interactions. Biochemistry. 19 (9) : 1774–1781 (1980).*
Schulman, L. H. Attachment of protein affinity–labeling reagents of variable length and amino acid specificity to $E.$ $coli$ tRNA.sup.fMet Nucleic Acid Research. 9 (5): 1203–1217 (1981).*
Eshaghpour et al. Specific chemical labeling of DNA fragments. Nucleic Acids Research 7 (6) : 1485–1495 (Aug. 1979).*
Yang et al. Covalent Attachment of Fluorescent Groups to Transfer Ribonucleic Acid Reactions with 4–Bromomethyl–7–methoxy–2–oxo–2H–benzopyran. Biochemistry 13 (17) : 3615–3621 (1974).*
Reines et al. A New Method for Attachment of Fluorescent Probes to tRNA. Methods in Enzymology, vol. LIX, [7], pp. 146–156 (1979).*
Landegent et al. 2–Acetylaminofluorene–modified Probes for the Indirect Hyrbridocytochemical Detection of Specific Nucleic Acid Sequences. Experimental Cell Research 153 : 61–72 (1984).*
Hopman et al. Bi–color detection of two target DNAs by non–radioative in situ hybridization. Histochemistry, 85 : 1–4 (1986).*

* cited by examiner

Primary Examiner—Ethan Whisenant
(74) Attorney, Agent, or Firm—William E. Murray

(57) ABSTRACT

Direct label probe compositions which stain DNA of a preselected single chromosome or region of a chromosome of a multi-chromosomal genome are provided that comprise mixed DNA segments which are covalently bound to fluorophore groups through linking groups. The mixed DNA segments are derived from the DNA present in the preselected chromosome or chromosome region. These probe compositions can be used concurrently or sequentially with other probe compositions.

16 Claims, No Drawings

METHODS FOR MULTIPLE DIRECT LABEL PROBE DETECTION OF MULTIPLE CHROMOSOMES OR REGIONS THEREOF BY IN SITU HYBRIDIZATION

RELATED APPLICATIONS

This application is a CON of Ser. No. 09/110,562 filed Jul. 6, 1998, now U.S. Pat. No. 6,277,569; which is a DIV of Ser. No. 08/781,682 filed Jan. 10, 1997, now U.S. Pat. No. 5,776,688; which is a CON of Ser. No. 08/476,694 filed Jun. 7, 1995, now U.S. Pat. No. 5,663,319; which is a DIV of Ser. No. 08/222,167 filed Apr. 4, 1994 now U.S. Pat. No. 5,491,224; which is a CON of Ser. No. 07/762,913 filed Sep. 19, 1991, now abandoned; which is a CIP of Ser. No. 07/585,876, filed Sep. 20, 1990, now abandoned.

FIELD OF THE INVENTION

The present invention relates to the detection and identification of chromosomes or regions of chromosomes by hybridization of a multiplicity of different chromosome-specific probes. In particular, this invention relates to in situ hybridization of these chromosome specific probes to the target chromosome. The present invention also relates to the detection of chromosomes or regions of chromosomes using fluorescently labeled reagents.

Background of the Invention

Probes containing DNA sequences which are complementary to target DNA sequences of specific individual whole chromosomes or regions of chromosomes of a multi-chromosomal genome are known (see, for example, Pinkel et al. in "Fluorescence in situ hybridization with human chromosome-specific libraries: Detection of trisomy 21 and translocations of chromosome 4" at *Proc. Nat'l Acad. Sci. USA* 85:9138–9142, December 1988; Manuelidis in "Chromosomal Localization of Complex and Simple Repeated Human DNA's" *Chromosoma* 66:23–32, 1978).

The vast majority of prior art probes prepared from such sequences were indirect label probes and so required post-hybridization processing. Thus, for example, such probes were derivatized with biotin, and, following the hybridization procedure, steps were pursued to build a sandwich-like structure of fluorescein-labeled avidin and biotinylated anti-avidin antibodies. In contrast, the direct label probes of this invention require only one probe penetration step of a slide mounted specimen during an in situ hybridization procedure.

Prior art methods for labeling such prior art chromosome-specific complementary DNA sequences present difficulties in controlling the number of label moieties attached to individual sequences.

Improved probe compositions comprised of (a) fluorophore labels which are easily and accurately directly detected, and (b) DNA segments which are complementary to specific chromosomal DNA segments would be very useful as chromosome specific stains in in situ hybridization assays. The present invention provides both such probes and efficient, reliable methods for their preparation and use.

SUMMARY OF THE INVENTION

The present invention provides: (1)probe compositions for the in situ detection of a chromosome or a region of a chromosome, (2)methods for the preparation of such probe compositions, and (3)methods for the use of such probe compositions for the in situ detection of a chromosome or a region of a chromosome.

This invention provides probe compositions for in situ detection of a preselected chromosome or region of a chromosome comprising multiple DNA segments complementary to different portions of the chromosome or chromosome region to be detected where, in the probe compositions, DNA segments include multiple fluorescent labels covalently linked thereto.

The invention includes a probe composition that contains unhybridized DNA segments which are essentially complementary to DNA base sequences existing in different portions of the chromosome or chromosome region to be detected and which contain a plurality of cytosine bases (i.e., deoxycytidine nucleotides). A number of the cytosine bases have a fluorescent label covalently bonded thereto. The number of fluorescently labeled cytosine bases is sufficient to generate a detectable fluorescent signal while the individual so labeled DNA segments essentially retain their specific complementary binding (hybridizing) properties with respect to the chromosome or chromosome region to be detected.

The invention also includes a method for making a probe composition for in situ detection of a particular preselected chromosome or a region of such chromosome comprising:

(a) disrupting (that is, fragmenting) DNA complementary to the chromosome, or the region of the chromosome, into fragments, (b) transaminating the DNA fragments, and (c) covalently linking a fluorescent dye to the transaminated DNA fragments.

More specifically, the invention includes a method for preparing a probe composition for in situ detection of a preselected chromosome or region of a chromosome comprising:

(a) transaminating with a linking group a number of deoxycytidine nucleotides contained in unhybridized DNA base sequences or segments that are essentially representative of complementary base target sequences existing in the chromosome or chromosome region to be detected; and (b) covalently bonding a fluorescent label to at least a portion of the transaminated deoxycytidine bases, the portion of deoxycytidine bases having fluorescent labels covalently bonded thereto being sufficient to generate a detectable fluorescent signal while essentially retaining the specific complementary binding properties of the transaminated bases with respect to the chromosome or the chromosome region to be detected.

In addition, the invention provides a method for in situ detection of a preselected chromosome or a region of the chromosome comprising:

(a) adding an excess of blocking DNA to an inventive probe composition preferably under hybridizing conditions to bond with nonspecific binding DNA in the probe composition, thereby forming a blocked probe composition, (b) contacting the blocked probe composition under hybridizing conditions with the chromosome or the chromosome region to be detected, and (c) detecting the binding of the blocked probe composition to the chromosome or the chromosome region to be detected by fluorescent techniques.

It is an additional object of the present invention to provide probe compositions that are directly labeled with fluorescent dyes. The use of such directly labeled probe compositions avoids the need for detailed and lengthy post-hybridization procedures as required by the indirectly labeled prior art probe compositions using, for example, biotin labels, avidin, and biotinylated antiavidin antibodies. The inventive probe compositions permit the user to proceed immediately from the hybridization step to final washing and visualization, thereby reducing the necessary amount of assay time and labor. The number of reagents required to perform the assay is also reduced, resulting in enhanced simplicity of use and manufacturing.

It is a specific object of the present invention to provide a probe composition for the in situ detection of a preselected chromosome or a preselected region of a chromosome wherein the probe composition contains multiple DNA segments that are complementary to different portions of the chromosome or the chromosome region to be detected. The multiple DNA segments in the probe composition include multiple fluorescent labels that are covalently linked to the DNA segments. These fluorescent labels permit the DNA segments that hybridize with the chromosome or the chromosome region to be detected using fluorescent techniques. In a preferred embodiment, the fluorescent labels are covalently linked to a number of the deoxycytidine bases in the DNA segments through linking groups. The number of deoxycytidine bases having fluorescent labels is sufficient to generate a detectable fluorescent signal, while at the same time the specific binding properties of the labeled DNA segments are essentially retained with respect to the chromosome or the chromosome region to be detected.

It is also an object of this invention to detect preselected multiple chromosomes or regions of chromosomes. This is accomplished by labeling one library of DNA segments specific for one chromosome or chromosome region with one fluorescent label and labeling another library of DNA segments specific for another chromosome or chromosome region with another fluorescent label, such that the fluorescent labels can independently be detected by fluorescent techniques. DNA segments of each chromosome or chromosome region of interest are thus so labeled. Thus, combinations of such resulting probe compositions of this invention can be used to detect two or more chromosomes or regions of chromosomes.

This invention also comprises a method for detecting a plurality of preselected chromosomes or regions of chromosomes, by providing a probe composition of such labeled specifically binding DNA segments for each chromosome or region of chromosome of the preselected plurality. The probe composition specific to each chromosome or chromosome region is labeled with a different fluorescent label such that each fluorescent label can be detected in the presence of the others. These probe compositions of labeled DNA are then contacted either in admixture or in succession under hybridizing conditions with the chromosomes or the regions of the chromosomes to be detected. Hybridization is detected by the presence or absence of the particular fluorescent signal generated by each of the labeled DNA segments which has hybridized with the particular selected chromosome or the particular selected chromosome region.

The detection of multiple chromosomes or chromosomal regions is considerably more difficult using an indirect labeling technique since different indirect binding partners (e.g. biotin/avidin or antibody/antigen) are required for each chromosome or region to be identified. For example, detection of two different chromosomes would require biotin/avidin and a specific antibody/antigen binding pair, in addition to two different detectable labels, such as fluorophores. The indirect label technique, therefore, requires six label components as compared to only two label components required by the direct label technique. The detection of three events requires the addition of a third different set of antibody/antigen partners and a third fluorophore (nine label components total compared to three components in the direct label technique). It is much more difficult to find and adapt an additional pair of binding partners than it is to find an additional fluorophore. A large number of fluorophores are commercially available in reactive forms amenable to labeling transaminated DNA.

It is an additional specific object of the present invention to provide preferred methods for making probe compositions for the in situ detection of a preselected chromosome or preselected region of a chromosome. The first step of a preferred inventive method is to disrupt plasmid DNA derived from a phage chromosomal library into fragments. These DNA fragments are transaminated with a linking group and fluorescent dyes are then covalently linked to the transaminated DNA fragments. In a preferred embodiment of the present invention, the number of transaminated deoxycytidine nucleotides to which fluorescent labels are covalently bonded is sufficient to generate a detectable fluorescent signal while at the same time the specific binding properties of the DNA segments are essentially retained with respect to the chromosome or chromosome region to be detected.

It is a further specific object of the present invention to provide preferred methods for the in situ detection of a preselected chromosome or preselected region of a chromosome. In general, the preferred methods are carried out by contacting a probe composition of the present invention with the preselected chromosome or chromosome region to be detected under hybridizing conditions. The presence or absence of the fluorescent signal generated by a probe composition that has been hybridized with the chromosome or the chromosome region of interest is then detected. In a preferred embodiment, an excess of blocking DNA is added to the probe composition preferably under hybridizing conditions, thereby forming a blocked probe composition. This blocking DNA binds with nonspecific binding DNA in the probe composition. The blocked probe composition is then contacted with the chromosome or chromosome region of interest under hybridizing conditions.

Further objects and preferred embodiments of the present invention are discussed in the following description of the preferred embodiments and claims.

DETAILED DESCRIPTION (A) Definitions

The term "sequence" refers to a chain or interconnected series of DNA nucleotides.

The term "fragment", "segment" or "DNA segment" indicates generally only a portion of a larger DNA polynucleotide or sequence such as occurs in one chromosome or one region of a chromosome. A polynucleotide, for example, can be broken up, or fragmented into, a plurality of segments or fragments. As is known, a chromosome characteristically contains regions which have DNA sequences that contain DNA repeated segments. The term "repeated" has reference to the fact that a particular DNA segment occurs a plurality (i.e., at least two) of times as the same DNA sequence, or plurality of DNA sequences. Individual DNA segment size and/or DNA repeated segment size can vary greatly. For example, in the case of the human genome, each DNA repeated segment is now believed to be typically in the approximate size range of about 5 to about 3,000 bp.

Illustratively, a single chromosome alphoid DNA sequence may incorporate at least about five different DNA repeated segments.

The term "genome" designates or denotes the complete, single-copy set of genetic instructions for an organism as coded into DNA of the organism. In the practice of the present invention, the particular genome under consideration is typically multi-chromosomal so that such DNA is cellularly distributed among a plurality of individual chromosomes (which number, for example, in humans 22 pairs plus a gender associated XX pair or an XY pair).

In the practice of this invention, the genome involved in any given instance is preferably from a primate, and the DNA sequences of a preselected chromosome from such a genome contain DNA repeated segments that are inclusive of either alphoid DNA or are associated with the centromere of the preselected chromosome. As used herein, the term "alphoid" or "alpha satellite" in reference to DNA has reference to the complex family of tandemly repeated DNA segments found in primate genomes. Long tandem arrays of alpha satellite DNA based on a monomer repeat length of about 171 base pairs are located principally at the centromeres of primate chromosomes.

The term "chromosome" refers to a heredity-bearing gene carrier of a living cell which is derived from chromatin and which comprises DNA and protein components (especially histones). The conventional internationally recognized individual human genome chromosome numbering identification system is employed herein. The size of an individual chromosome can vary from one type to another with a given multi-chromosomal genome and from one genome to another. In the case of the (preferred) human genome, the entire DNA mass of a given chromosome is usually greater than about 100,000,000 bp. For example, the size of the entire human genome is about $3\times10^9$ bp. The largest chromosome, chromosome no. 1, contains about $2.4\times10^8$ bp while the smallest chromosome, chromosome no. 22, contains about $5.3\times10^7$ bp (Yunis, J. J. *Science* 191:1268–1270 (1976), and Kavenoff, R., et al. *Cold Spring Harbor Symposia on Quantitative Biology* 38:1–8 (1973)).

The term "region" indicates a portion of one chromosome which contains DNA repeated segments that are preferably alphoid or associated with the centromere. The actual physical size or extent of such an individual region can vary greatly. An exact quantification of such a region cannot now be made for all possible regions. Usually, a region is at least large enough to include at least one DNA sequence that (a) incorporates a plurality of copies of at least one DNA repeated segment and that (b) is identifiable and preferably enumeratable optically by fluoroscopic microscopic examination after formation of fluorophore labeled hybrids in such region following an in situ hybridization procedure with a direct label probe or probe composition. Presently available information suggests that a region may contain more than a single such DNA sequence with each such DNA sequence containing one or more DNA repeated segments.

The term "region" is typically and characteristically a chromosome fragment which comprises less DNA mass or size than the entire DNA mass or size of a given chromosome. As is known, not all the DNA of a given chromosome or chromosome region is arranged as DNA sequences comprised of or containing DNA repeated segments. A region, for example, can have a size which encompasses about $2\times10^6$ to about $40\times10^6$ DNA bp. which size region encompasses, for example, centromeres of the human chromosomes. Such a size is thus a substantial fraction of the size of a single human chromosome. Such a region size is presently preferred as a region size in the practice of this invention although larger and smaller region sizes can be used. A centromeric region of even a small human chromosome is a microscopically visible large portion of the chromosome, and a region comprising DNA repeated segments (not alphoid or centromeric) on the Y chromosome occupies the bulk of the chromosome and is microscopically visible. In general, the term "region" is not definitive of a particular one (or more) genes because a "region" does not take into specific account the particular coding segments (exons) of an individual gene. Rather, a "region" as used herein in reference to a chromosome is unique to a given chromosome by reason of the particular combination of DNA segments therein for present probe composition formation and use purposes.

The term "centromere" refers to a heterochromatic region of the eucaryotic chromosome which is the chromosomal site of attachment of the kinetochore. The centromere divides just before replicated chromosomes separate, and so such holds together the paired chromatids.

The term "gene" designates or denotes a DNA sequence along a chromosome that codes for a functional product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" or "probe composition" refers to a polynucleotide, or a mixture of polynucleotides, such as DNA sequence(s) or DNA segment(s) which has (or have) been chemically combined (i.e., associated) with individual label-containing moieties. Each such polynucleotide of a probe is typically single stranded at the time of hybridization to a target.

The term "label" or "label containing moiety" refers in a general sense to a moiety, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent).

Probe compositions of this invention contain DNA segments that are chemically bound to label-containing moieties. Each label-containing moiety contains at least one fluorophore (fluorescent) group, and each label-containing moiety is derived from a monofunctional reactive substituent-containing, and also fluorophore substituent containing, starting fluorescent compound, as hereinbelow more particularly described.

The term "direct label probe" (or "direct label probe composition") designates or denotes a nucleic acid probe whose label after hybrid formation with a target is detectable without further reactive processing of hybrid. Probe compositions of this invention are of the direct label type.

The term "indirect label probe" (or "indirect label probe composition") designates or denotes a nucleic acid probe whose label after hybrid formation with a target must be further reacted in subsequent processing with one or more reagents to associate therewith one or more moieties that finally result in a detectable entity.

The term "target", "DNA target" or "DNA target region" refers to one nucleotide sequence which occurs at a specific chromosomal location. Each such sequence or portion is typically and preferably at least partially single stranded (i.e. denatured) at the time of hybridization. When the target nucleotide sequences are located only in a single region or fraction of a given chromosome, the term "target region" is sometimes applied. Targets for hybridization can be derived from specimens which include but are not limited to chromosomes or regions of chromosomes in normal, diseased or malignant human or other animal or plant cells, either interphase or at any state of meiosis or mitosis, and either extracted or derived from living or postmortem tissues, organs or fluids; germinal cells including sperm and egg cells, seeds, pollen or zygotes, embryos, chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to semen, blood, hair or other samples.

The term "hybrid" refers to the product of a hybridization procedure between a probe and a target. Typically, a hybrid is a molecule that includes a double stranded, helically configured portion comprised of complementarily paired single stranded molecules, such as two DNA molecules, one of which is a target DNA nucleotide sequence, and the other of which is the labeled DNA nucleotide sequence of a probe.

The term "stain", "selective stain", "selectively stained" or equivalent refers generally to a localized area color achieved by a staining procedure or the like which color takes effect on a selected group of components (or constituents) of a cytological or histological preparation. Typically, such colored components are to undergo a microscopic examination, or the like. Commonly another or other supplementary or background color (i.e., stain) may be involved, such as a so-called counterstain which takes effect on all components of a larger class within which a selectively stained group of components falls. The main purpose of a stain is to enhance or make possible identification of components during such an examination. A probe composition of this invention under hybridizing conditions produces hybrids which in effect stain a target chromosome or target chromosomal region with a fluorophore group.

The term "fluorescent" (and equivalent terms) has general reference to the property of a substance (such as a fluorophore) to produce light while it is being acted upon by radiant energy, such as ultraviolet light or x-rays.

The term "fluorescent compound" or "fluorophore group" generally refers to an organic moiety. A fluorescent compound is capable of reacting, and a fluorophore group may have already reacted, with a linking group. A fluorescent compound may include an organic chelator which binds a luminescent inorganic ion such as a rare earth like terbium, europium, ruthenium, or the like.

The term "linking compound" or "linking group" as used herein generally refers to a hydrocarbonaceous moiety. A linking compound is capable of reacting, and a linking group may have already reacted, with a nucleotide sequence (or nucleotide segment). A linking compound is also capable of reacting, and a linking group may have already reacted, with a fluorophore compound.

The term "in situ" means that the chromosomes are exposed from the cell nucleus without substantial disruption or relocation of the chromosomes with respect to each other and with the chromosomes being accessible to fluorescently labeled DNA probes.

The term "denaturation" or "denature" has reference to the at least partially complete conversion of a polynucleotide from a multi-stranded (or double-stranded) state to a single stranded state. The presence of an agent or agents which in effect lowers the temperature required for denaturation and for subsequent hybridizing conditions between probe (or probe composition) and target is generally desirable, and a presently most preferred such agent is formamide. Using, for example, about 50:50 volume ratio mixture of water and formamide, an illustrative temperature for thermal denaturation is in the range of about 70 to about 80 degrees C. applied for times that are illustratively in the range of about 1 to about 10 minutes.

The term "in situ hybridization" has reference to hybridization of a probe to a target that exists within a cytological or histological preparation or specimen. As a result of an in situ hybridization procedure, hybrids are produced between a probe and a target. This term "in situ hybridization" may be inclusive of denaturation and may also be inclusive of a hybrid or probe detection procedure which is practiced after in situ hybridization of a probe to a target. A specimen can be adhered as a layer upon a slide surface, and a specimen can, for example, comprise or contain individual chromosomes or chromosome regions which have been treated to maintain their morphology under, for example, denaturing conditions, or conditions such as typically exist during a flow cytometric analysis in a probe detection procedure. The term "in situ hybridization" may include use of a counterstain. In the case of the inventive fluorophore labeled probes or probe compositions, the detection method can involve fluorescence microscopy, flow cytometry, or the like.

The term "hybridizing conditions" has general reference to the combinations of conditions that are employable in a given hybridization procedure to produce hybrids, such conditions typically involving controlled temperature, liquid phase, and contacting between a probe (or probe composition) and a target. Conveniently and preferably, at least one denaturation step precedes a step wherein a probe or probe composition is contacted with a target. Alternatively, a probe can be contacted with a specimen comprising a DNA target region and both subjected to denaturing conditions together as described by Bhatt et al. in *Nucleic Acids Research* 16: 3951–3961. Using, for example, about a 50:50 volume ratio mixture of water and formamide, an illustrative temperature for contacting and hybridization between probe (or probe composition) and target is in the range of about 35 to about 55° C. applied for a time that is illustratively in the range of about 1 to about 18 hours. Other hybridizing conditions can be employed. The ratio of numbers of probes to number of target sequences or segments can vary widely, but generally, the higher this ratio, the higher the probability of hybrid formation under hybridizing conditions within limits.

The term "complete", "completely", "substantially complete" or "substantially completely" refers to the capacity of a direct label probe composition of this invention to hybridize with a target so that the target body or bodies is/are highlighted and identifiable (by a fluorescence microscope, a flow cytometer, or the like) after hybridization therewith to an extent at least sufficient to show (i.e., stain or identify) the target's full extent (morphology). Thus, variations in fluorescence coloration intensity may sometimes be present (i.e., observed) in an individual hybridized chromosomal target body, but the target body as a whole is substantially highlighted.

The term "lower" refers to an individual compound, group or radical means that such compound, group or radical contains less than 6 carbon atoms.

The term "paint probe" or "painting probe", (or "paint probe composition" or "painting probe composition") refers to a probe or probe composition, such as a probe composition of this invention, which is adapted to hybridize under hybridizing conditions with a target which comprises one predetermined (i.e., preselected) chromosome of a multichromosomal genome. If only a fractional part of such one chromosome happens to be present in a specimen undergoing such a hybridization with such a probe composition, then such fractional part so hybridizes and is identified. Typically, one paint probe of this invention can be admixed with a second so as to make possible the simultaneous staining and detection of two predetermined chromosomes.

The term "clone", "cloning" or equivalent refers to the process wherein a particular nucleotide segment or sequence is inserted into an appropriate vector, the vector is then transported into a host cell, and the vector within the host cell is then caused to reproduce itself in a culturing process, thereby producing numerous copies of each vector and the respective nucleotide sequence that it carries. Cloning results in the formation of a colony or clone (i.e., group) of identical host cells wherein each contains one or more copies of a vector incorporating a particular nucleotide segment or sequence. The nucleotide segment or sequence is now said to be "cloned", and the product nucleotide segments or sequences can be called "clones".

The term "blocking DNA" or "blocking DNA composition" refers to a DNA which has the capacity, under hybridizing conditions, to hybridize with nonspecific binding DNA present in a probe. A blocking DNA composition is comprised of a mixture of DNA segments that are derived from, include, and are preferably representative of, the total genomic DNA of a multi-chromosomal genome that is under consideration and which incorporates a target. Such segments can, for example, be prepared by fragmenting (as taught herein) DNA sequences comprising or representative of such total genomic DNA, and such DNA segments so prepared are complementary to DNA segmental portions occurring throughout the chromosomes (including the regions) of this genome, such segments can also be prepared, for example, from a total genomic DNA, by other procedures, such as by a procedure involving the procedural steps of denaturing partially reannealing or re-hybridizing, and treating with enzymes, thereby to reduce the quantity of non-repeated segments therein. Blocking DNA is at the time of use with a probe composition preferably in the form of segments having average sizes in the range of about 150 to about 600 base pairs.

The term "library" is used herein in its conventional sense to refer to a set of cloned DNA fragments which together represent an entire genome or a specified fragment thereof, such as a single chromosome. Various libraries are known to the prior art and are available from various repositories, and techniques for genome and genome fragment preparation, and for cloning libraries therefrom, are well known. A present procedural preferences is to fragment a selected one chromosome that was separated by flow sorting or the like. Fragmentation prior to cloning is preferably achieved by digestion with restriction endonucleases or the like. This procedure produces fragment ends which are particularly amenable to insertion into vectors. However, those skilled in the art will appreciate that any conventional or convenient technique for fragmentation can be used. The fragments are then conventionally cloned to produce a chromosome library.

The term "blocked probe composition" has reference to a probe composition of this invention which is in admixture with a blocking DNA composition.

The term "diluent DNA" or equivalent refers to DNA which is the same as, or is similar to the DNA that is incorporated into a particular probe composition of this invention. Diluent DNA, when admixed with transaminated polynucleotides that constitute an intermediate in the making of a probe composition of the invention, or when admixed with a product probe composition of this invention, functions to dilute the total number of labeled DNA segments that are present in a given volume or weight of a probe composition of this invention.

As those skilled in the art will appreciate, a diluent DNA can also sometimes function as a blocking DNA, and vice versa.

The term "carrier DNA" refers to DNA which functions to reduce the amount of probe DNA which is inherently lost due to such effects as absorption of probe DNA to adjacent surface portions, such as the surface portions of a container vessel wherein a probe is being stored, the surface portions of a glass slide whereon a specimen undergoing in situ hybridization is deposited, or the surface portions of cellular debris present in a specimen undergoing in situ hybridization, or the like. Carrier DNA is comprised of DNA derived from an unrelated genomic species, such as salmon sperm in admixture with DNA segments derived from the human genome. A carrier DNA may be optionally added to a hybridization solution that incorporates a probe of this invention.

The term "nonspecific binding DNA" refers to DNA which is complementary to DNA segments of a probe and which DNA occurs in at least one other position in a genome, which other position is outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

(B) Starting Materials (1) The Starting Chromosomal DNA

When starting chromosomal DNA is used in the practice of this invention, such is typically and preferably in the form of one or more DNA sequences which taken together contain a multiplicity of DNA segments that individually occur at various locations in and throughout an individual preselected chromosome of a given multi-chromosomal genome and that are reasonably representative of DNA occurring in the preselected chromosome. Although in its naturally occurring state, a starting DNA sequence typically has a size much greater than about one million base pairs, at the time of availability for use as a starting material in the practice of this invention, the starting DNA sequence may already be somewhat fragmented, depending upon such factors as the methods used in separation, isolation and the like. A presently preferred genome is the human genome.

For purposes of preparing a given probe composition of this invention, the starting chromosomal DNA sequence(s) can be obtained by various techniques. Thus, such can be derived or obtained, for example, from (a) DNA that is separated by flow sorting a plurality of a single preselected chromosome of a multi-Chromosomal genome which DNA is preferably purified from component intracellular material of an organism; (b) a chromosome library of a preselected chromosome, and (c) an inter species hybrid which incorporates DNA of a preselected chromosome. A presently preferred starting chromosomal DNA is a chromosome library of a preselected chromosome which library has been prepared by standard methods and is available from traditional sources known to those in the art, such as the American Type Culture Collection (ATCC) or other repositories of human or other cloned genetic material. While a large number of specific chromosome libraries are available from the ATCC, representative libraries are shown in Table I:

TABLE I

HUMAN CHROMOSOME LIBRARIES

| Human Chromosome Library | ATCC No. | Human Chromosome Library | ATCC No. |
|---|---|---|---|
| 1 | 57738 | 13 | 57757 |
| 1 | 57753 | 14 | 57739 |
| 1 | 57754 | 14 | 57706 |
| 2 | 57716 | 14/15 | 57707 |
| 2 | 57744 | 15 | 57729 |
| 3 | 57717 | 15 | 57740 |
| 3 | 57748 | 15 | 57737 |
| 3 | 57751 | 16 | 57765 |
| 4 | 57719 | 16 | 57730 |
| 4 | 57718 | 16 | 57749 |
| 4 | 57700 | 16 | 57758 |
| 4 | 57745 | 17 | 57741 |
| 5 | 57720 | 17 | 57759 |
| 5 | 57746 | 18 | 57742 |
| 6 | 57721 | 18 | 57710 |
| 6 | 57701 | 19 | 57731 |
| 7 | 57722 | 19 | 57766 |
| 7 | 57755 | 19 | 57711 |
| 8 | 57723 | 20 | 57732 |
| 8 | 57707 | 20 | 57712 |
| 9 | 57724 | 21 | 57743 |
| 9 | 57705 | 21 | 57713 |
| 10 | 57725 | 22 | 57733 |
| 10 | 57736 | 22 | 57714 |
| 11 | 57726 | X | 57750 |
| 11 | 57704 | X | 57734 |
| 12 | 57727 | X | 57752 |
| 12 | 57736 | X | 57747 |
| 13 | 57728 | Y | 57735 |
| 13 | 57705 | Y | 57715 |

The ATCC deposits of Table I are available from the American Type Culture Collection, 12301 Parklawn Drive, Rockville, Md.

The invention contemplates that such chromosome specific DNA sequences can also be synthesized in vitro by any one of a number of enzymatic means known to those skilled in the art. Specific single chromosomal DNA sequences usable as starting material in the practice of the invention are isolatable from one or more of these sources by methods which are well known to those skilled in the art.

Examples of prior art teachings illustrating the preparation of suitable starting sequences for making whole chromosome paint probes of this invention include (but are not limited to):

1. Chromosomes are physically separated, fragmented, and the fragments propagated as clones, as in: M. A. Van Dilla, et al. in Bio/Technology 4, 537–552 (1986) and Cox, D. R. et al. in Science 250, 245–250 (1990).

2. An entire chromosome is physically scraped from the surface of a microscope slide, fragmented, and the fragments propagated as clones, using the technique described in: Ludecke, H. J. et al. in Nature 338: 348–350 (1989).

3. Single human chromosomes are propagated in rodent cell lines. Thus, the entire DNA content of such a line is fragmented, and the fragments propagated as clones. A method for the generation of human, monochromosomal hybrid lines is described in: Carlock, L. R. et al. in Somatic Cell Mol. Genet. 12: 163–174 (1986).

4. Sequences from purified single chromosome preparations are enzymatically amplified by utilizing primer oligonucleotides complementary to any of a number of abundant, polydisperse repeated DNA sequences which are present at many locations along the chromosome. Purified chromosomal preparations from methods 1, 2 or 3 above are subjected to amplifications of the type described in: Nelson D. L. et al. in Proc. Natl. Acad. Sci. USA 86: 6686–6690 (1989).

(2) The Starting Regional Chromosomal DNA

When starting regional chromosomal DNA is used in the practice of this invention, such is typically and preferably derived either directly or indirectly from one preselected region of one preselected chromosome of a genome which is preferably multi-chromosomal. Such starting regional chromosomal DNA is typically in the form of at least one DNA sequence. It is presently preferred that each such sequence or sequences incorporate a plurality of at least one DNA repeated segment and preferably a plurality (i.e., at least two) of structurally differing DNA repeated segments. Preferably, such regional DNA sequence is unique relative to other regions of the total genome. The starting regional DNA incorporates a multiplicity of DNA segments that occur individually at various locations in and throughout the individual preselected region of one chromosome and that are reasonably representative of DNA occurring in the preselected region. A presently preferred genome is the human genome.

At the time of involvement in the methodology of this invention, such an individual DNA regional sequence may be in pieces or fragments, but the sum of the fragments would equal a whole naturally occurring DNA sequence. Such an individual starting DNA sequence can be and preferably is a cloned or otherwise produced copy of a naturally occurring regional sequence. Such a starting sequence can have a size which is only a fraction of the size of the naturally occurring whole DNA sequence that is present in the preselected region. However, a given starting regional chromosomal DNA is reasonably representative of DNA present in the preselected region.

Various regional chromosomal DNA (and their preparation methods) sequences are known to the prior art and such can be used as starting DNA sequences in the preparation of fluorophore group direct label probe compositions of this invention, and various known techniques can be used to obtain or prepare such a starting regional chromosomal DNA.

Examples of prior art teachings illustrating methods for obtaining suitable starting regional DNA sequences that incorporate DNA repeated segments include (but are not limited to):

5. Sequences are obtained from cloned pools of DNA enriched in repeat DNAs, as described in; Manuelidis, L., Chromosoma 66: 23–32 (1978), in Yang, T. P. et al. in Proc. Natl. Acad. Sci. USA 79: 6593–6597 (1982), and in Moyzis, R. K. et al., in Chromosoma 95: 375–386 (1987).

6. Sequences obtained from purified single chromosome preparations are enzymatically amplified by utilizing primer oligonucleotides complementary to conserved portions of chromosome-specific repeated DNA sequences. Purified chromosomal preparations from methods 1, 2 or 3 above are subjected to amplifications of the type described in: Koch, J. E., et al. in *Chromosoma* 98: 259–265 (1989).

7. Sequences obtained from the preparation procedure described in copending application Bittner et al. U.S. Ser. No. 07/762,912, published as PCT Patent Application WO 93/0246, on Apr. 1, 1993, filed on even date herewith. The teachings of this application are incorporated herein by reference. Such sequences are presently preferred for use in the present invention.

Examples of prior art teachings illustrating methods for obtaining starting DNA sequences which are suitable for making chromosomal regionally specific probes of this invention include (but are not limited to):

8. Many sequences specific for particular regions of a human chromosome have been determined. A publicly available compilation of such sequences is maintained by the National Institute of Health, see: Bilofsky, H. S. et al. in *Nucl. Acids Res.* 16: 1861–1864 (1988). There are currently 5141 individual sequence entries in this compilation. There are 6,182,990 base-pairs of sequence information presently provided in these entries.

9. The physical location of many anonymous DNA segments on the human chromosome have been described, see: Donis-Keller, H. et al. in *Cell* 51: 319–337 (1987).

10. Known sequences or DNA segments (references 8 and 9 above) are used as the starting point for obtaining further sequences which are linked to the available sequence by screening plasmid, cosmid, bacteriophage or yeast artificial chromosome libraries as described in: Wahl, G. M., et al. in *Proc. Natl. Acad Sci. USA* 84: 2160–2164; Williams, B. G. et al. 1979 in *J. Virol* 29: 555–575 (1982), and Brownstein, B. H. et al. in *Science* 244: 1348–1351 (1989).

11. Cloned sequences from regions of chromosomes for which there is no known linkage to an already determined sequence are obtained by micro-dissection of that region followed by fragmentation, amplification and cloning, as in; Ludecke, H. J., et al. in *Nature* 338: 348–350 (1989), or by enzymatic amplification of human DNA in interspecific radiation hybrids which contain less than a complete human chromosome, as in Cox, D. R., et al. in *Science* 250: 245–250 (1990).

For purposes of preparing a direct label probe composition of the invention, it is presently preferred to employ a starting chromosomal DNA that is representative of the DNA of a selected chromosome or chromosomal region.

In general, a starting chromosomal DNA, or a starting regional chromosomal DNA, is not required to have DNA segments which have the same distribution, or occurrence frequency that is characteristic of the DNA segments that naturally (or normally) occurs. By using, for example, a starting chromosomal DNA, or regional chromosomal DNA, wherein the occurrence or distribution of DNA repeated segments is skewed, the capacity of a product probe composition to selectively stain target chromosomal DNA completely is not destroyed, but rather may be altered. The result is that, in a resulting hybridized target in a specimen, the stained chromosomal DNA which is present in a target region may appear to be unevenly stained, but that target region is still substantially completely and selectively stained. The subregions within a stained target displaying greatest coloration intensity when subsequently examined under a fluorescence microscope are believed to correspond to target chromosomal subregions wherein the relative frequency of occurrence of segmental DNA occurring in the probe composition is greater than at locations where the coloration is weakest. A starting DNA with a skewed distribution of DNA segments compared to a normal or naturally occurring distribution of DNA segments can be used for test or evaluation purposes, if desired.

The nature, structure and size of individual starting DNA sequences, the number of the different sequences utilized, and the like variables associated with a starting chromosomal or regional chromosomal DNA cannot be stated in absolute terms because of inherent variations in the genome from one organism to another, and because the composition of a starting DNA sequence population for a given genome can vary from one source to another, and even from one batch to another of a particular starting DNA taken from the same source. However, after fragmentation of a starting DNA, is achieved, for example, as hereinbelow described, the starting DNA is preferably converted to a mixture of DNA segments which mixture comprises segments that are approximately and reasonably representative of the entire selected chromosome or chromosomal region, and that are preferably distributed throughout such chromosome or region.

The characteristic complexity of a given starting DNA, however, is presently considered to be desirable from the standpoint of the present invention since such complexity tends to make possible direct label probe compositions of the invention which can be prepared from different starting DNA from the same selected chromosome or region, yet such product probe compositions behave in a substantially identical manner as regards staining capacity. A starting chromosomal or regional DNA typically contains about 18 to about 25 mole percent deoxycytidine nucleotides based on the total number of deoxynucleotides present therein.

(3) The Starting Linking Compound

A starting linking compound employed in the practice of this invention is a difunctional organic compound, that is, such contains two substituent functional (i.e., reactive) substituents per starting linking compound molecule.

At least one of such functional substituents per linking compound molecule is reactive with deoxycytidine nucleotides in a polynucleotide under bisulfite catalyzed aqueous transamination conditions (such as provided herein, for example). Examples of such substituents include alkyl amino (primary and secondary), hydrazido, semicarbazido, thiosemicarbazido, and the like. Amino groups are presently most preferred.

When the amino group is secondary, the secondary substituent is preferably a lower alkyl group, but other non-blocking such secondary substituents can be used, if desired.

The second of other of such two functional substituents per linking compound molecule is reactive with a third functional substituent which is itself incorporated into a starting fluorescent compound (as herein described). Such second functional substituent can itself be either blocked or unblocked. When the second substituent is unblocked, then it is substantially non-reactive with other substances that are present in the transamination medium (especially polynucleotides) during transamination. When the second substituent is blocked then it is substantially non-reactive with the other substances that are present in the transamination medium (especially polynucleotides) during transamination.

Examples of suitable unblocked second functional substituent group include amino, carboxyl, phosphate, sulfonate, hydroxyl, hydrazido, semicarbazido, thiosemicarbazido and the like. Presently, most preferred unblocked second functional substituent include amino (primary or secondary) and carboxyl groups.

The carboxyl group preferably is either in the salt form or in the acid form, but can sometimes be in the ester form. When in the salt form, presently preferred cations are alkali metals, such as sodium and potassium.

Examples of suitable blocked second functional substituent group include blocked sulfonate, blocked phosphate, blocked sulfhydryl, and the like.

Examples of suitable blocking substituents include lower alkyl groups such as methyl, ethyl, propyl, etc.

The first and the second functional substituents are interconnected together through a linker (or linking) moiety. This linking moiety can have any convenient structure but such is non-reactive with other substances that are present in the transamination medium during transamination. A present preference is that the linking moiety be a hydrocarbonaceous divalent group which is acyclic or cyclical and which can optionally incorporate other atoms.

The two functional substituents present in such a difunctional linking compound can be respective substituents of the linking moiety. Such substituents can be on adjacent carbon atoms relative to each other, or they can be spaced from one another in a linking compound molecule by a plurality of intervening interconnected atoms (preferably carbon atoms). Preferably these functional groups are in an alpha, omega relationship to one another (that is, each is at a different opposite end region) in a given linking compound molecule.

Thus, the two functional radicals in a linking compound are each bonded to an organic linking group moiety which is either entirely hydrocarbonaceous (that is, composed only of carbon and hydrogen atoms), or is comprised of carbon and hydrogen atoms plus at least one additional atom or group which contains at least one atom selected from the group consisting of oxygen, sulfur, nitrogen, phosphorous, or the like. Preferably such additional atom(s) are so associated with such organic moiety as to be substantially less reactive than either one of such above indicated two functional radicals that are present in a given starting linking compound. Hydrocarbonaceous organic moieties that are saturated aliphatic are presently preferred, and more preferably such moiety is a divalent alkylene radical containing from 2 through 12 carbon atoms, inclusive. However, if desired, such a saturated aliphatic radical can incorporate either at least one ether group (—O—) or at least one thio-ether group (—S—), but it is presently more preferred that only one of such ether or thio ether groups be present. It is presently preferred that a linking compound incorporates an organic radical that contains at least two and not more than about a total of about 20 carbon atoms, although more carbon atoms per molecule can be present, if desired.

Presently preferred are linking compounds in which each of such functional radicals is an amino radical. Both acyclic and cyclic diamino compounds can be used.

Examples of suitable aliphatic primary diamines include alkylene primary amines wherein the alkylene group is propylene, butylene, pentylene, hexylene, nonylene, and the like.

Examples of suitable aliphatic secondary diamines include $CH_3NH(CH_2)_2NH_2$, $CH_3NH(CH_2)_2NHCH_3$, and the like.

Diamino compounds incorporating hydroxylated hydrocarbons can be used. Examples of acyclic such compounds include 1,3-diamino-2-hydroxypropane; 1,4-diamino-2,3-dihydroxybutane; 1,5-diamino-2,3,4-trihydroxypentane; 1,6-diamino-1,6-dideoxy-D-mannitol (or D-glucitol or D-galactitol), 1,6-diamino-2,3,4,5-tetrahydroxy hexane, and the like.

Examples of suitable polyhydroxylated cyclic dimensions include cis or trans cyclic diamino compounds where the diamines are constrained in a ring, such as 1,4-diamino-2,3,5,6-tetrahydroxy cyclohexane, cis and trans 1,2-diaminocyclohexane, cis and trans 1,2-diaminocyclopentane, and hydroxylated derivatives thereof, such as 1,2-diamino-3,4,5,6-tetrahydroxycyclohexane, 1,2-diamino-3,4,5-trihydroxy cyclopentane, 3,6-diamino-3,6-dideoxy-derivatives of myo-inositol, such as

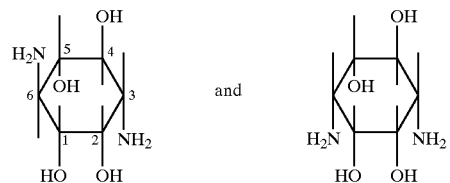

and the like.

Examples of suitable heterocyclic diamines include piperazine, N,N'-bis(3-aminopropyl) piperazine, derivatives thereof, and the like.

Examples of suitable ether-group containing diamines include 3-oxo-1,5-pentanediamine, 3,6-dioxo-1,8-diaminooctane, and the like.

Examples of suitable linking compounds containing both an amino radical and a carboxyl radical include amino acids, such as sarcosine (N-methylglycine), and alpha amino acids, such as glycine, alanine, glutaric acid, aspartic acid, proline, pipecolinic acid (piperidine-2-carboxylic acid), isopipecolinic acid (piperidine-4-carboxylic acid), glucosaminic acid and derivatives thereof, and the like.

Examples of alpha, omega aminocarboxylic acids (in addition to the above identified amino acids) include 4-aminobutyric acid, 6-aminohexanoic acid, 8-aminooctanoic acid, and the like.

Examples of phosphorous containing difunctional linking compounds include alpha, omega aminoalkyl phosphoric acid, monoesters, such as 0-(2-aminoethyl) phosphate disodium salt and the like.

Examples of suitable sulfur containing difunctional linking compounds include alpha, omega aminoalkyl sulfonic acids, such as taurine (2-amino-ethyl sulfonic acid) and the like.

One presently more preferred class of difunctional linking compounds is represented by the following generic formula:

$$H-N(R_1)-R-X-H \tag{1}$$

wherein:

X is a divalent radical selected from the class consisting of:

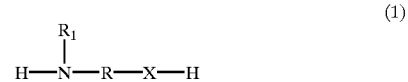

wherein:

R is an alkylene radical containing from 2 through 12 carbon atoms inclusive, or of per-hydroxylated carbocyclic ring, and $R_1$ and $R_2$ are each independently selected from the class consisting of hydrogen and lower alkyl.

Preferably, in Formula (1), R contains not more than 7 carbon atoms,

X is

and $R_1$ and $R_2$ are each hydrogen, and R contains less than 7 carbon atoms.

Mixtures of different linking compounds can be used, such as linking compounds containing a mixture of mono and/or diamines, but such mixtures are not preferred because of associated problems in transamination control and usage.

Diamines which are characterized by having a large proportion thereof that exists as a free unprotonataed species at pH values of about 7 appear to enhance the present transamination reaction. Ethylene diamine (pK of about 7.6) is presently most preferred for use as the reactive difunctional amine because of this property.

When, for example, such a linking compound is bonded to a DNA sequence using a transamination reaction, as hereinbelow described, the transamination reaction is carried out so that an amino radical in the linking compound bonds to the sequence or segment. Then, in the resulting linking group, one functional group remains free to undergo further reaction. Thus, when the second functional radical is an amino radical, such radical remains free thereafter to undergo further reaction with the fluorescent compound, as hereinbelow described. When the second functional radical is a carboxyl radical, such radical remains free thereafter to undergo such a further reaction with the fluorescent compound, as hereinbelow described.

(4) The Starting Fluorescent Compound

The starting fluorescent compounds employed in the practice of this invention each incorporate at least one fluorophore substituent (or group) per molecule and also one functional (i.e., reactive) substituent (or group) per molecule.

The functional substituent is chosen so as to be reactive with the second functional substituent remaining incorporated into a linking group in a transaminated polynucleotide (such as is prepared as described herein.) The linking group is derived from a linking compound (as above described).

For example, in a starting fluorescent compound, the reactive substituent can be chosen to be reactive with an amino substituent (as above defined), or with a carboxyl substituent which is in the acid or the salt form (as above defined).

For purposes of reactivity with such an amino substituent in a linking group (using a reaction as hereinbelow described), the reactive substituent of the fluorescent compound can be a convenient amine-reactive functionality, such as a carboxyl substituent that is in the acid or salt form (such as above defined), an aldehyde radical or the like. A presently preferred such reactive substituent is selected from, and exemplified by, the group consisting of isothiocyanates, N-hydroxysuccinimide esters, sulfonyl chlorides, carboxylic acid azides and the like.

For purposes of reactivity with such a carboxyl substituent in a linking group, the reactive substituent of the fluorescent compound can be a convenient carboxyl-reactive functionality, such as an amino substituent which is in a primary or a secondary form (such as above defined) or the like. A presently preferred such reactive substituent is a primary amino substituent.

The reactive substituent can also sometimes be, for example, a thiol, a phosphate ester, or the like, the choice, depending upon the nature of the reaction substituent that is present in a linking group.

In general, any fluorophore substituent or group can be employed in a starting fluorescent compound. If more than one fluorophore substituent per fluorescent compound is used, then it is presently preferred that each fluorophore substituent be similar or identical in structure to others thereof in a single fluorescent compound. A present preference is to employ fluorescent compounds containing about 1 to about 3 fluorophore substituents per fluorescent compound molecule and most preferably a fluorescent compound contains only one fluorophore substituent per fluorescent compound molecule.

Preferably, a starting fluorescent compound has a molecular weight which is not more than about 5000 and more preferably not more than about 1000 because larger molecular weights may possibly have an adverse effect upon the hybridization capacity of a product probe with a complementary target sequence.

For reasons of detectability, it is presently preferred that a starting fluorescent compound and the fluorophore groups therein have an extinction coefficient of at least about 6,000 $M^{-1}$ $cm^{-1}$ (and preferably at least about 10,000 $M^{-1}$ $cm^{-1}$) in the wavelength region of the excitation light incident on a given specimen, and also a quantum yield of at least about 0.02. The term "extinction coefficient" is used herein in its conventional sense to mean the absorbance of a 1 molar (M) solution of the fluorescent compound contained in a 1 centimeter (cm) path length cuvette. Similarly, the term "quantum yield" is used herein in its conventional sense to mean the number of photons emitted by a fluorophore per the number of photons absorbed by that fluorophore.

Exemplary and presently preferred starting fluorescent compounds are shown in Table II below.

TABLE II

EXEMPLARY STARTING FLUORESCENT COMPOUNDS[1]

1. 7-amino-4-methylcoumarin-3-acetic acid, succinimidyl ester (AMCA)
2. sulforhodamine 101 sulfonyl chloride; also known by the name Texas Red ™ or Texas Red ™ sulfonyl chloride (Tx Rd)
3. 5-(and-6)-carboxyrhodamine 101, succinimidyl ester; also known by the name 5-(and-6)-carboxy-X-rhodamine, succinimidyl ester (CXR)[2]
4. Lissamine rhodamine B sulfonyl Chloride (LisR)
5. 5-(and-6)-carboxyfluorescein, succinimidyl ester (CFI)[2]
6. fluorescein-5-isothiocyanate (FITC)[2]
7. 7-diethylaminocoumarin-3-carboxylic acid, succinimidyl ester (DECCA)
8. tetramethylrhodamine-5-(and-6)-isothiocyanate (TRITC)[2]
9. 5-(and-6)-carboxytetramethylrhodamine, succinimidyl ester (CTMR)[2]
10. 7-hydroxycoumarin-3-carboxylic acid, succinimidyl ester (HCCA)
11. 6-[fluorescein-5-(and-6)-carboxamido]hexanoic acid (FCHA)[2]
12. N-(4,4-difluoro-5,7-dimethyl-4-bora-3a,4a-diaza-3-indacenepropionic acid, succinimidyl ester; also known by the name 5,7-dimethylBODIPY ®propionic acid, succinimidyl ester (DMBP)
13. "activated fluorescein derivative" (FAP); this compound consists of a fluorescein nucleus connected through a spacer group to an N-hydroxysuccinimide ester reactive group and desgnated as "FAP" by the manufacturer, Molecular Probes, Inc.
14. eosin-5-isothiooyanate (EITC)[2]
15. erythrosin-5-isothiocyanate (ErITC)[2]
16. Cascade ™ Blue acetylazide (CBAA); which is the O-acetylazide derivative of 1-hydroxy-3,6,8-pyrenetrisulfonic acid

[1]Abbreviations used to refer to these compounds are enclosed within parentheses. For some coumpounds alternative names, including trademarked names, are provided. ™ refers to trademarks of Molecular Probes, Inc. The term "succinimidyl ester" refers to the ester formed between a carboxylic acid substituent of the fluorophore and N-hydroxysuccinimide, and is also referred to as an "N-hydroxysuccinimide ester" or an "N-hydroxysuccinimidyl ester" or an "NHS ester".
[2]Certain fluorescein and rhodamine derivatives contain reactive substituents (carboxy or isothiocyanate) attached to either the 5- or 6-positions. These compounds can be obtained as mixtures of the two isomers, designated as "5-(and-6)", or in some cases as the purified isomers. The labeling and fluorescent properties are not expected to vary greatly between isomers or between a specific isomer and the mixture. The isomers or mixtures designated above were those used in labeling experiments (see Examples).

All fluorescent compounds in Table II were obtained from Molecular Probes, Inc. Eugene, Oreg.

As those skilled in the art will readily appreciate, a starting fluorescent compound is preferably selected for use in making a given product probe composition which will produce, under conditions of fluorophore excitement in a single specimen, emitted light of a color which contrasts with the color of the light emitted by the fluorophore group-containing label portion of any concurrently or sequentially used other probe or probe composition which is targeted to the same or related karyotype, such as a genome, a specific chromosome, or a specific region of a chromosome, or the like that is within the genome involved.

(C) Probe Production (1) General

Primarily because of their characteristically relatively large typical size and also their random size characteristics, the individual starting polynucleotides. (which typically have average sizes the range of about 50 to about 4000 bp) of a the starting specific chromosome, or chromosomal regions tend to display relatively poor hybrid forming capacity (after being labeled).

Also, previously known prior art chemical synthetic methods for joining label moieties to a nucleotide sequence, particularly a fluorophore-containing label moiety, tend to result in problems of controlling the location and the number of label moieties per sequence, and also in problems of sequence alteration. These problems can adversely affect the resulting probe hybridization capacity with the desired selected chromosomal target materials, and also, ultimately, the detection by staining of specific chromosomal DNA present in a specimen.

It has now been discovered that these problems can be overcome, and that a direct label probe composition of excellent hybrid forming capacity and probe performance characteristics exists for preselected individual chromosome or chromosome region selective staining purposes in in situ hybridization, when a probe composition is comprised of a mixture of DNA segments such as is described herein wherein the segments are specific to a preselected chromosome or a preselected chromosome region, and wherein the segments are chemically bound to fluorophore groups through linking groups.

Various procedures can be employed to prepare such a probe composition. A presently preferred and illustrative preparation procedure is now described in which the following procedural steps are carried out:

(a) Fragmenting (i.e., disrupting) DNA sequences that are specific to one preselected chromosome or preselected chromosome region into DNA fragments (or segments);

(b) Transaminating deoxycytidine nucleotides existing in the sequences (and consequently also in the derived segments) with a linking compound (as above described); and (c) Covalently linking (i.e., bonding) residual radicals of the so produced transaminated linking groups with a fluorescent compound (as above described).

While step (b), or steps (b) and (c), can precede step (a), it is presently preferred for step (a) to precede step (b). In the following description, the foregoing (a), (b), (c) step sequence order is used for present organization purposes.

Other combinations and variations of such step sequences are also feasible for use in preparing a probe composition of this invention. For example, one can covalently bond the fluorescent compound to the linking compound, then transaminate and finally fragment the DNA sequences (using step conditions similar to those herein provided); however, this procedure tends to result in low yields due to the lower solubility of the fluorophore group in the transamination reaction.

(2) Fragmenting

The DNA segments are derived from a particular preselected starting chromosomal DNA or starting regional chromosomal DNA (as above characterized) by fragmenting. Before fragmenting, the starting DNA preferably has an average size polynucleotide of at least about 150 bp. After fragmenting, the DNA segments preferably have an average size that is within a range of about 150 to about 600 bp with a presently more preferred average size being about 200 to about 400 bp, and a presently most preferred average segment size being about 300 bp. Each of these segment fragments is believed to be complementary to a segmental portion existing in one or more DNA sequences which occur in the particular preselected chromosome or preselected chromosome region.

The number of fragments derived from fragmenting such starting specific chromosomal or regional chromosomal DNA sequences in any given instance is unknown, probably variable from one batch to another, and large. Also, the structure of the nucleotide sequences of the individual fragments is unknown and probably variable from one batch to another. In fact, a mixture of such segments from DNA sequences of a single chromosome contains thousands, if not tens of thousands, of differently structured segments. For reasons associated with the capacity of a product probe composition to stain DNA of an individual preselected chromosome or chromosome region, and the brightness of the fluorescence in hybrids formed therewith, it is presently believed to be desirable to utilize DNA fragments having a relatively uniform average size in the ranges above indicated.

As those skilled in the art will readily appreciate, these DNA fragments can be formed from starting specific chromosomal DNA sequences by various known techniques, including, for example, enzyme treatment, as with restriction enzymes, or polymerases, limited DNase I digestion, limited mung bean nuclease digestion, sonication, shearing of DNA in a French press, shearing of DNA through a narrow-gauge needle, and the like.

However, it is presently greatly preferred to form such DNA fragments by sonication of a starting specific chromosomal DNA. Sonication can be carried out by any convenient procedure. Presently preferred sonication conditions utilize an aqueous dispersion of starting specific chromosomal DNA that is preferably in the range of about 0.05 to about 4 mg per ml, although smaller and larger such concentrations can be employed. The ultrasonic frequency applied is preferably in the range of about 20,000 cycles per second and is applied for a total time in the range of about 1 to about 10 minutes with the tube containing the sample preferably immersed in a cooled bath to reduce heating of the sample. Suitable cooled baths include ice baths and baths containing dry ice and ethanol. Energy density applied to the DNA sequence material undergoing such ultrasonic processing is variable. For example, in the case of a Branson Sonifier Model 450 (Danbury, Conn.) with the microtip located about 2 to about 5 mm from the bottom of the tube in an aqueous solution, a suitable output power is in the range of about 25 to about 30 watts. Preferably, such ultrasonic energy is applied using about an 80% on time, and, correspondingly, about a 20% off time, for a total time of about 5 minutes, such as below exemplified herein.

Preferably, the starting specific chromosomal DNA is fragmented before the component sequences are subjected to transamination.

Regardless of the method of fragmenting, the result of fragmenting the plurality of sequences comprising specific chromosomal DNA is to produce a profusion of fragments of such starting DNA sequences. This profusion comprises DNA segments that individually occur at each one of a plurality of different locations in an individual preselected chromosome or chromosome region. The fragmented DNA segments are thus mixtures that are derived from the sequential starting DNA and that are approximately representative thereof.

Obviously, if the starting chromosomally or regionally specific DNA is obtained, for example, from a commercial source in an already suitably fragmented state, then a separate fragmenting step is not needed before a subsequent transaminating processing step is undertaken.

(3) Transamination

In the transamination, a minor fraction of the total deoxycytidine bases that are contained in the starting specific chromosomal DNA sequences and segments thereof become transaminated with an amino group of a difunctional linking compound (as above described) in the carbon 4 (C-4) atom position of the amino group of cytosine sites (i.e., deoxycytidine nucleotides). The extent of such transamination is such that between about 1 and about 30 mole percent of all deoxycytidine nucleotides that are present in a starting mixture of DNA segments that is representative of total genomic DNA of a given genome are thus substituted by such a linking group, and preferably about 2 to about 24 mole percent thereof. Expressed alternatively, about 0.2 to about 8 mole percent of all nucleotides contained in such a mixture of starting DNA sequences or DNA fragments are thus transaminated and preferably about 0.5 to about 6 mole percent. All such transaminations involve substantially only deoxycytidine nucleotides.

The most effective percentage of amination in any given instance is typically influenced by the particular fluorescent label moiety used. Since the average number of base pairs present in a sequence is preferably at least about 150, as above indicated, each sequence is thus preferably substituted by at least about one such linking group during the transamination procedure, as desired. Transamination to a greater extent seems to increase the potential for adversely affecting the specificity of product probes (subsequently) labeled with some fluorophores, such as FITC and TXRd, for example. High amination levels do not affect as greatly the specificity of CTMR and DECCA labeled probes, for example. Transamination to a lesser extent seems to adversely affect the brightness of fluorescent light generated in detecting product hybrids.

The transamination is conveniently accomplished under aqueous liquid phase conditions in the presence of a bisulfite catalyst. The concentration of DNA sequences (or segment fragments) is conveniently in the range of about 0.1 to about 1 mg per ml, the concentration of bisulfite anions is conveniently in the range of about 0.4 to about 1.4 moles per liter, the concentration of linking compound is conveniently in the range of about 1 to about 5 moles per liter, the pH is conveniently in the range of about 4.5 to about 8.0, the temperature is conveniently in the range of about 20 to about 45° C., and the contacting time is typically and exemplarily in the range of about 3 to about 72 hours (depending upon the amination level desired).

In the present transamination procedure, the bisulfite is conveniently introduced in the form of an alkali metal salt, with sodium and potassium being preferred alkali metals.

At the time of transamination, the linking compound is dissolved in the aqueous transaminating medium.

Preferably before, and also during the transamination, the DNA sequences or segments are preferably denatured, for example, by a preliminary boiling of DNA sequences or segments in water, such as for a time of about 1 to about 10 minutes followed by chilling to a temperature below about 4° C. (presently preferred), or by carrying out the transamination in the presence of a chaotrope, or by a combination of both procedures.

7. Sequences obtained from the preparation procedure described in copending application Bittner et al. U.S. Ser. No. 07/762,912, published as PCT Patent Application WO 93/0246, on Apr. 1, 1993, filed on even date herewith. The teachings of this application are incorporated herein by reference. Such sequences are presently preferred for use in the present invention.

The complexity of a DNA fragment mixture is illustrated and exemplified by the extent of amination achieved after a preliminary denaturing of the mixture DNA fragments by boiling. Since transamination only occurs at an appreciable rate on single stranded DNA, and since the reformation rate is slow in proportion to the complexity of the DNA, the specific chromosomal DNA is found to aminate to a lesser extent than is characteristic for a relatively more complex DNA mixture.

During the transamination with the bisulfite catalyst, reaction variables as above identified can be varied within the ranges indicated to achieve a desired degree of transamination with a given linking compound reactant.

The present transamination reaction is carried out or continued until a desired extent of transamination of the starting DNA sequence or segment mixture is obtained. In general, the maximum extent of transamination is determined by the level of transamination which causes, or begins to cause, either an adverse effect upon the complementary character of the nucleotide sequence or segments involved, or an increase in the amount of non-specific association of the subsequently labeled probe with non-target DNA or other cellular components, such as exist in a specimen, slide preparation or the like, during an in situ hybridization using a probe composition of this invention. There is evidently typically and preferably present in a transaminated product only a low mole percentage of totally unlabeled DNA sequences. The minimum level of transamination achieved in any given instance is determined by the objective of achieving substantially complete staining of a preselected chromosome or region of a chromosome should such be present in a given specimen. Even low amination levels do provide such result.

Low levels of amination may be desired so that after staining, a preselected chromosome or region of a chromosome can be observed without obscuring another stain (and associated specimen bodies) present in a given specimen.

The intensity of a specific chromosomal stain achievable in a specimen with a specific chromosomal staining probe composition of this invention can be readily regulated or reduced, if desired, so as to achieve a desired stain coloration intensity in a given specimen or the like. Such a reduction can be achieved by various techniques, such as, for example, (a) by lowering the extent of linking group transamination, thereby ultimately reducing the quantity of labeled nucleotide per unit weight that are present in a staining probe composition of this invention, (b) by diluting a transaminated mixture with a starting unlabeled DNA segment mixture, thereby introducing a diluent DNA into the probe composition, (c) by reducing the amount of probe present in a given hybridization solution, or the like. The fluorescent intensity of a labeled probe composition can be reduced by the addition of a preferably fragmented (as above described herein) unlabeled starting total genomic DNA thereto, such genomic DNA being of the genome from which the preselected chromosome was taken, prior to the time when fluorescent compound bonding is performed (as below further described).

The minimum level of transamination practiced in any given instance is conveniently determined by the desire to transaminate at least a predetermined mole percentage of the total deoxycytidine nucleotides present in the starting DNA, such as a fragmented DNA segment mixture.

A mixture resulting from a transamination procedure that is in accord with the teachings of the present invention can be conventionally further processed. A present preference is to dialyze such a product mixture, against a dilute aqueous buffer, such as sodium borate, tris(hydroxymethyl) aminomethane (TRIS), or the like at a pH of about 8 using a conventional dialyzing membrane and ambient temperatures.

The resulting mixture of transaminated nucleotide sequences or segments is then conveniently precipitated from the so dialyzed mixture, and the sequence is then separated from the supernatant by filtration, centrifugation, or the like.

Enzymatic techniques for obtaining aminated DNA are described in Analytical Biochemistry 157:199–207 (1986). The transaminated DNA sequences are covalently linked to any of a number of fluorescent compounds that have a reactive functional group capable of covalent bond formation with the transaminated DNA sequence.

(4) Fluorescent Compound Bonding

A resulting transaminated and amine substituted nucleotide derivative is then available for covalently bonding with a reactive fluorophore substituent-containing fluorescent compound, such as above described, with such compound reacting with a terminal functional substituent associated with the residue of the linking compound (i.e., the linking group) that has now been transaminated into a deoxycytidine moiety as above described. The number of fluorophore substituent-containing fluorescent compounds thus reacted per sequence or segment molecule is easily controlled. Preferably, starting DNA sequences are fragmented before being bound to fluorophore groups. Consequently, in a product probe composition, the number of label groups per DNA molecule is regulatable, as desired. The nucleotide sequence of each segment in the resulting product probe composition is believed to be substantially identical to that existing in a starting DNA mixture except for the added presence of the transaminated linking groups and the covalently bonded fluorophore groups.

The covalent linking or bonding of fluorescent compound to a terminal radical of a linking group in, for example, transaminated DNA segments is conveniently carried out under aqueous liquid phase conditions using a temperature in the range of about 4 to about 50° C., a concentration of transaminated DNA in the range of about 10 to about 500 μg per ml, a near-neutral pH for reactions of N-hydroxysuccinimide esters (e.g., pH of about 6 to 8) and an alkaline pH for reactions of isothiocyanates and sulfonic acid chloride (e.g., pH 8.5–9.5) and a time which is typically and exemplarily in the range of about 2 to about 18 hours.

Typically and preferably, the quantity of the starting fluorescent compound present is sufficient to provide a substantial molar excess relative to the total quantity of linking groups that are estimated to be present in the transaminated DNA sequences. In any given situation, an optimized molar excess can be conveniently determined relative to the concentration of the transaminated deoxycytidine nucleotide residues present in the fragments.

While theoretically the amount of fluorescent labeling compound only needs to equal the amount of transaminated deoxycytidine in the probe DNA, an excess is usually greatly preferred since some of the fluorescent compound molecules react by other routes which do not lead to attachment of label to DNA, such as reaction with water (hydrolysis), thereby to render a labeling compound nonreactive with aliphatic amine groups. Excess labeling compound is also used to increase the rate of reaction with the transaminated deoxycytidine so that the reaction is complete in a shorter amount of time. A larger excess is required for labeling compounds more sensitive to hydrolysis, such as N-hydroxysuccinimide esters and sulfonic acid chlorides, relative to compounds less sensitive to hydrolysis such as isothiocyanates. While a small excess of labeling compound to transaminated deoxycytidines may lead to low percentages of probe labeling, a large excess of labeling compound can be advantageous in providing high labeling percentages. Labeling compound quantities in excess of that required to achieve complete labeling is not disadvantageous to the labeling reaction. Very high amounts of labeling compound, however, can lead to post-reaction purification problems since substantially all of the unreacted fluorescent compound should be removed prior to using the product probe composition in in situ hybridization or the like. Therefore, very large excesses of fluorescent compounds are to be avoided, such as excesses greater than about a 250 fold molar excess.

When, for example, the fluorescent labeling compound is a succinimidyl derivative (that is, an N-hydroxy succinimide ester of a carboxyl substituted fluorophore or the like), or a corresponding sulfonic acid chloride derivative, then the transaminated DNA sequences containing the residual linking compound are conveniently reacted with about a 100 to about a 200 fold molar excess of the fluorescent labeling compound, relative to the intermediate transaminated nucleotides. For convenience herein, it is assumed that about 5% of total nucleotides are transaminated.

When, for example, the fluorescent labeling compound is an isothiocyanate derivative, then the transaminated DNA sequences are conveniently reacted with about a 50-fold molar excess of the fluorescent labeling compound.

In the reaction which occurs, covalent bonding is believed to occur between the reactive group of a starting fluorescent compound and the terminal group of a transaminated linking group (derived from a linking compound) that is associated with a DNA sequence. Preferably, at least one terminal group of one linking group per molecule is reacted with the fluorescent compound employed. Typically, about 10 to about 100 mole percent of the terminal sites (or terminal functional substituents) of the linking groups are reacted (covalently bonded) and thus fluorescently labeled. The extent of reaction between linking groups and fluorescent compounds appears to be influenced by the nature of the fluorophore substituent(s) present in a particular fluorescent compound. Preferably, for efficiency reasons, at least about 70 mole percent of the linking groups of a given transaminated DNA composition are so labeled, and most preferably at least about 90 mole percent thereof are so labeled. Thus, in general, preferably about 0.3 to about 6 mole percent of the total nucleotides present in such a starting mixture of DNA segments are fluorescently labeled.

Residual labeling compound not covalently attached to the probes at the end of the reaction time can be removed by a variety of methods, such as precipitation of the DNA, gel permeation chromatography, affinity chromatography, dialysis, gel electrophoresis, and combinations of these methods. The number and types of procedures combined to purify labeled probes depends upon the size of the labeling compound, including the size of aggregates of these labeling compounds, and their ability to noncovalently bond with the labeled DNA, such as through ionic and hydrophobic interactions. One procedure which provides adequate removal of unreacted labeling compound involves an ethanol precipitation step followed by a gel permeation chromatography step followed by a second ethanol precipitation step. The resulting precipitated labeled probe can be dissolved in water to provide a stock solution of probe which may be used directly in in situ hybridization reactions when combined with the other hybridization components (e.g., formamide, dextran sulfate, buffer, and like known specific probe components).

The resulting reaction product of the transaminated DNA sequences and the selected fluorescent compound comprises a probe composition of this invention.

(D) Direct Label Probe Composition
(1) Probe Compositions

Thus, there is provided a class of direct label probe composition wherein DNA segments are bound to fluorophore groups. Such a probe composition considered as a unit is suitable for use in specific chromosomal or specific regional chromosome DNA staining and for detecting by in situ hybridization or the like the presence in a specimen of a DNA target region that is either a preselected chromosome or a preselected chromosome region, as the case may be. Such a probe composition contains a plurality of different DNA segments that individually occur throughout a preselected target region (either a single chromosome or a single chromosome region). These DNA segments are substituted on about 1 to about 30 mole percent of the total deoxycytidine nucleotides thereof with a linking group structure which initially retains a terminal functional (or reactive) group. At least about 10 mole percent of all such retained terminal functional groups have each been covalently bound to an individual fluorophore radical containing group. Individual ones of such so labeled plurality of DNA segments that thus comprise such a probe composition of this invention are hybridizable to complementary DNA segmental portions occurring in DNA sequences of the preselected target region.

Preferably, in a probe composition of this invention, this difunctional linking group is characterized by the formula:

(2)

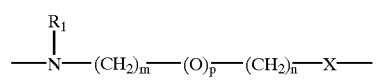

wherein:

X is selected from the divalent group consisting of:

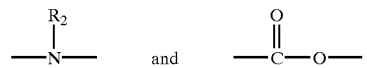

$R_1$ and $R_2$ are each independently selected from the group consisting of hydrogen and lower alkyl;

m and n are each an independently selected integer of 1 through 6 inclusive; and p is the integer 0 or 1, and wherein the group:

is transaminated to a deoxycytidine nucleotide of one said DNA segment and the group —X— is covalently bonded to one said label moiety.

Thus, a direct label probe composition of this invention comprises a mixture of DNA segments which are derived from, and are approximately a representation of, the DNA of a given preselected chromosome or a given preselected chromosome region. A presently preferred class of chromosomes comprise those of the human genome. The DNA segments of such a mixture are chemically bound through the intervening linking groups to fluorophore groups. The characteristics of probe compositions of this invention are summarized for convenience in Table III below:

TABLE III

Characteristics of Probe Compositions of the Invention

| | Ranges (approximate) | | |
|---|---|---|---|
| Variable | Broad | Preferred | Presently Most Preferred |
| 1. Mixture of DNA Segments | | | |
| 1.1 Individual segment average size in bp | 150–600 | 200–400 | about –300 |
| 1.2 Mole percent of all deoxycytidines in DNA segments substituted by linking group | 1–30 | 2–24 | 4–20 |
| 2. Difunctional linking group | | | |
| 2.1 No. of carbon atoms per group | 2–20 | 2–6 | about 2 |
| 2.2 No. of linking groups per DNA segment | 0.4–45 | 1–24 | 3–15 |
| 3. Flourophore group | | | |
| 3.1 No. of fluorophore radicals per flourophore group | 1–4.5 | about 1 | about 1 |
| 3.2 Mole percent of all linking groups substituted by fluorophore group | 10–100 | 70–100 | 90–100 |
| 3.3 No. of fluorophore per segment | 0.04–450 | 0.7–24 | 2.7–15 |

(2) Formulations of Probe Compositions

The probe compositions of this invention can be utilized, that is, made, sold, and used, in various forms, including dry solid form, aqueous solutions, and aqueous formulations that are adapted for direct usage in a hybridization procedure.

In aqueous media, a probe composition of the invention is preferably in a substantially completely dissolved form. As those skilled in the art of DNA probes will appreciate, the content of an aqueous formulation of a probe composition (including a hybridization solution) can vary widely depending upon many variables and objectives. For an illustrative example, one suitable class of hybridization solutions has a composition as characterized in Table IV below:

TABLE IV

Illustrative Class of Probe Composition Suitable For Use In In Situ Hybridization

| | Ranges (approximate) | |
|---|---|---|
| Component | Broad | Preferred |
| 1. Probe Composition of the Invention | 1–200 ng/μl<br>2–200 ng/μl paints<br>1–30 ng/μl cens | 5–60 ng/μl - paints<br>1–10 ng/μl - cens |
| 2. Denaturant | 0–8% (v/v) | 50–80% (v/v) |
| 3. Hybridization Rate Promoter | 0–15% (w/v) | 8–12% (w/v) |
| 4. Buffer Salt(s) | 5–100 mM | 10–50 mM |
| 5. Hybrid Stabilizer salt | 0.05 mM-1M | 0.2–0.5 M |
| 6. Blocking DNA | 0–10 μg/ml | 0.1–0.3 μg Cot-1 DNA<br>0.2–0.7 μg human placental DNA |
| 7. Water | Balance | Balance |

In such a probe composition of Table IV, the denaturant functions to promote denaturation of the DNA segments present in a probe composition. Such promoted denaturation is desirable because it lowers the temperature employed for denaturation and for hybridization. While the various denaturants known to the prior art can be employed, a presently most preferred denaturant is formamide.

Similarly, the various hybridization rate promoters known to the prior art can be used. A presently most preferred hybridization rate promoter is a dextran sulfate.

Similarly, the various water soluble buffer salts known to the prior art can be used. A present preference is to maintain the pH of a probe composition solution at a value that is in the range of about 5.5 to about 8.5. Buffer salts which are suitable for maintaining such a pH include, for example, citric acid, tris (hydroxymethyl) amino methane, phosphoric acid, and the like. A presently preferred buffer salt composition can comprise citric acid (or sodium citrate).

Similarly, a hybrid stabilizer salt which promotes stabilization of hybrids formed during a hybridization procedure is desirable. The hybrid stabilizer salts known to the prior art can be used, such as NaCl, KCl, $MgCl_2$, and the like. However, the presently most preferred such salt is sodium chloride.

The water used is preferably preliminarily distilled or deionized.

(3) Blocked Probe Compositions

An optional but preferred component of a probe composition such as shown in Table IV is a blocking DNA composition.

The use of a diluent DNA in the manufacture of a probe composition of the invention is above discussed (see the above subsection on transamination) as one means for regulating fluorescent intensity in a hybridized target. A diluent DNA can also function as a blocking DNA composition and as a means for regulating fluorescent intensity and hybridizing specificity. Blocked compositions of this invention are presently preferred. Presently preferred blocking DNA compositions for blocked probe compositions of this invention which are targeted to human chromosomes or regions of chromosomes include fragmented human placental DNA and Cot-1.

Cot-1 DNA is obtainable as catalog #52795A from Life Technologies, Inc., Gaithersburg, Md. Cot-1 DNA is reportedly prepared by the following procedure: Mechanically sheared total human genomic DNA is fragmented to an average sequence size of less than 400 bp. This material is denatured, and then hybridized for a period sufficient to render large fractions of the highly repeated DNA sequences thereof double-stranded. The mixture of double and single-stranded DNA species are then treated (digested) with nuclease S1, a nuclease which specifically degrades single stranded DNA to mono- and oligo-nucleotides. Undigested double-stranded Cot-1 DNA is recovered from this mixture. Cot-1 DNA is reportedly in the form of segments having an average size of about 191 bp.

Thus, such a useful starting blocking DNA class is derived from a total genomic DNA, which has been denatured, partially reannealed or re-hybridized, and treated with enzymes, or otherwise processed, to reduce the amount of naturally occurring non-repeated segments therein, by processes known to the prior art.

The total weight of blocking DNA composition that is admixed with a given probe composition of the invention is preferably in excess of the total weight of the probe composition. A resulting mixture of a probe composition of this invention and a blocking DNA composition can optionally be subjected to hybridizing conditions for a period of time before subsequently being used for hybridization with a target and selective staining. Alternatively one can, if desired, directly use a denatured blocked probe composition for hybridization with a target under hybridizing conditions.

A blocking DNA admixed with a probe composition of this invention prevents repetitive common DNA segments in large part from hybridizing with chromosomal DNA of a preselected chromosome or chromosomal region present in a specimen. Blocked probe composition are beneficial because staining selectively is improved, for example, when specific chromosomal probe preparations are being used in combination with other specific probe compositions.

Thus, repetitive sequences in such a specific blocked probe composition are prevented form hybridizing to the same repetitive sequence that occurs in, for example, non-targeted chromosomes. Such a hybridization also occurs when the blocking DNA composition is present at the time when a blocked probe composition of this invention is being hybridized under hybridizing conditions with a target. The hybridization of blocking DNA composition DNA segments to target complementary segmental regions probably also occurs. The effect of such hybridizations is to regulate the intensity of the fluorescence produced by a given probe composition after hybridization to a target composition. The quantity of blocking DNA composition present is now believed to be inversely related to the hybrid intensity observed after hybridization; however, there appear to be many variables influencing the relationship.

The compositions of Table IV can be prepared, if desired, from preliminarily prepared precursor compositions which are admixed together at the time of usage in a hybridization procedure. Such precursor compositions can be referred to as a "kit".

(E) In Situ Hybridization and Staining (1) General

Probe compositions of this invention are well suited for use in hybridization procedures as stains for respective preselected chromosomes or chromosome regions.

The invention thus provides a process for identifying a preselected chromosome or chromosome region present in a specimen. The process involves the three sequential steps of (a) contacting a specimen believed to contain such a chromosome or chromosome region (including fragments thereof) under hybridizing conditions with a probe composition of the invention which will hybridize with the target DNA of a chromosome or chromosome region to produce hybrids between the target DNA and the probe DNA segments present in the probe composition, (b) separating from the resulting specimen residual portions of the probe composition, and (c) examining the resulting specimen.

The specimen examining can be variously accomplished, for example, with a fluorescent microscope, a flow cytometer, or the like. Examination involves irradiating the resulting specimen with energy which is at least sufficient to cause fluorophore groups present in the hybrids to fluoresce while concurrently detecting the resulting fluorescent energy so produced. As those skilled in the art will appreciate, depending upon the particular objectives and conditions utilized, this process of examining or identifying can be practiced without the separating step if the level of residual probe composition is so low as not to interfere with the examination.

(2) Slide Staining

Advantageously, any convenient or particular in situ hybridization procedure can be used in the practice of this aspect of the present invention. An in situ hybridization procedure can involve a particular specimen which contains all or only a fraction of the preselected chromosome or chromosome region.

Currently, a present preference is to use a probe composition of this invention in in situ hybridization procedures of the type that are commonly and conveniently carried out on specimens which have preliminarily been prepared and mounted on a slide, such as a slide comprised of glass or the like. Conventional slide preparation procedures can be employed, such as taught, for example by: F. T. Bosman et al. in *Genetica* 5: 425–433 (1975); and Gall et al. in *Proc. Natl. Acad. Sci. USA* 64: 600 (1969); and conventional in situ hybridization procedures can be employed, such as taught, for example, by B. Bhatt et al. in *Nucleic Acids Research* 16: 3951–3961 (1988); A. H. N. Hopman et al. in *Experimental Cell Research* 169: 357–368 (1987); NcNeil et al. in *Genet Anal Techn Appl* 8: 41–58 (1991); and Tkachuk, D. C. et al. in *Genet Anal Techn Appl* 8: 67–74 (1991).

To accomplish DNA staining of a preselected chromosome or chromosome region in such a slide mounted and processed specimen using a probe composition of this invention, the following illustrative procedure can be carried out.

Preferably, such slide mounted specimen is preliminarily processed to dehydrate at least partially and also denature at least partially the DNA that is presumed to be present therein. Conventional denaturing and dehydrating procedures can be employed, such as exemplified in the Embodiments below provided. Thereafter, a sequential hybridization step sequence typically is carried out under hybridizing conditions. First, the slide mounted specimen is contacted with the probe composition of this invention.

Next, the combination of the specimen and the treating probe composition that is in contact therewith are subjected to an incubation period which is typically and preferably in the range of about 60 to about 1,000 minutes, though longer and shorter incubation period times can be employed, if desired. During the incubation period, the temperature is preferably maintained in the above indicated range of about 30 to about 45° C. During this incubation period, the treating probe composition undergoes hybridization with the genomic DNA that is present in the specimen.

Next, the resulting hybrid-containing specimen is subjected to a liquid washing procedure that is adapted to separate therefrom unreacted, residual treating probe composition. Advantageously, washing procedures similar to those known to the prior art of in situ hybridization can be used (for example see Bhatt et al in *Nucleic Acids Research* 16: 3951–3961 (1988)). Usually several different wash baths are employed which contain NaCl, buffer salts, such as sodium citrate, and the like, and formamide, at various concentrations. Higher formamide concentrations and lower NaCl concentrations are used for higher stringency (greater ability to remove residual probe DNA). Also detergents can be used, especially in the last bath. Stringency is also increased by raising the temperature of the wash baths above room temperature.

After soaking in a last wash bath or the like, the slide is allowed to drain preferably in a near vertical position and to be fully or partially air-dried prior to subsequent adding of a mounting medium and covering with a coverslip. The mounting medium (usually a solution) conventionally contains glycerol, buffer salts, and an antifade material which reduces the rate of photo-oxidation of the fluorophore labels, as those skilled in the art will appreciate. A chemical type counterstain can be incorporated into the mounting medium.

The slides can be viewed after processing immediately under a fluorescence microscope and conventional filters, or they can be stored at room temperature for several days or the like before examination.

The resulting slide mounted specimen can be further hybridized with other probe preparations. For example, the coverslip can be removed, the slide can be soaked (immersed) in one of the wash baths to remove surface deposits of the mounting medium. A preferably denatured second probe hybridization solution is then applied (as above described) to the slide (the slide is not denatured a second time), the resulting slide is incubated to facilitate hybridization, and then the slide is washed, as described above.

In the case of examining a specific chromosomally stained specimen produced from a probe composition of this invention, as those skilled in the art will appreciate, the particular filter used is preferably one which is matched to the spectral response characteristics associated with the particular fluorophore that is involved as the label moiety in a given probe composition of this invention. Such a filter either is commercially available, or is readily made by conventional filter-making or filter assembly technology. The following Table V presents illustrative specifications for filters and such filters were used with the fluorophores included in the Examples herein presented:

TABLE V

FLUORESCENCE MICROSCOPE FILTER SET NOMINAL SPECIFICATIONS

| | Filter Set | | | |
|---|---|---|---|---|
| Fluorophore | Excitation Filter† | Dichroic Beamsplitter‡ | Emission Filter† | Filter Set Ref. # |
| AMCA/ | BP 365 (>50)* | 395 | LP 420 | 1 |
| DAPI | BP 360 (50)** | 400 | BP 450 (50) | 2 |
| CBAA | BP 360 (50)** | 400 | BP 425 (35) | 11 |
| HCCA | BP 400 (20)** | 440 | BP 456 (28) | 12 |
| DECCA | BP 435 (20)** | 475 | BP 535 (45) | 3 |
| | BP 432 (20)** | 455 | BP 478 (32) | 13 |
| FITC | BP 470 (40)* | 510 | LP 520 | 4 |
| | BP 485 (20)* | 510 | BP 540 (50) | 5 |
| | BP 480 (30)** | 505 | BP 535 (45) | 6 |
| | BP 496 (24)** | 515 | BP 532 (28) | 14 |
| CFI | (same as for FITC) | | | |
| DMPB | (same as for FITC) | | | |

TABLE V-continued

FLUORESCENCE MICROSCOPE FILTER SET NOMINAL SPECIFICATIONS

| Fluorophore | Excitation Filter† | Dichroic Beamsplitter‡ | Emission Filter† | Filter Set Ref. # |
|---|---|---|---|---|
| FCHA | (same as for FITC) | | | |
| FAP | (same as for FITC) | | | |
| EITC | BP 518 (26)** | 545 | BP 558 (30) | 15 |
| ErITC | (same filters as EITC, although not optimal for this fluorophore - should be shifted to longer excitation and emission wavelengths relative to EITC) | | | |
| TRITC | BP 546 (12)* | 580 | LP 590 | 7 |
|  | BP 540 (23)** | 570 | BP 605 (55) | 8 |
| CTMR | (same as for TRITC) | | | |
| LisR | (same as for TRITC or Tx Rd) | | | |
| Tx Rd | BP 560 (40)** | 595 | BP 635 (60) | 9 |
|  | (same as for Tx Rd) | | | |
| Propidium iodide | BP 540 (23)** | 565 | BP 615 (30) | 10 |

†Wavelength values are listed in units of nanometers. Bandpass filters are marked "BP" with the center of the filter's transmission band listed first and the full width at half maximum enclosed in parenthesis. Long pass filters are marked "LP" with the transition region between low and high transmission indicated.
‡Wavelength values are listed in units of nanometers and indicate the region of the filter's transition between high reflectance and high transmission.
*Filter set obtained from Zeiss.
**Filter set obtained from Omega Optical.

Those skilled in the art will appreciate that in in situ hybridization of a slide mounted specimen, the sequence of (a) contacting and (b) separating (as above indicated) can be advantageously carried out more than once before the step (c) (examining) as above indicated is carried out. In each such repeat of steps (a) and (b) (each of which is conveniently carried out as above described herein), a different probe composition is employed, with a probe composition of this invention being employed on one repeat, and with another (different) probe composition being employed in each of the other repeats, each such other probe composition being targeted to a different predetermined fractional region of said genome.

(3) Flow Cytometry

The specific chromosomal staining probe compositions of this invention can also be used, for another example of utilization, in a procedure utilizing fluorescence activated flow cytometry. For example, initially chromosomes can be conventionally isolated, for instance, from mitotic cells of a cell culture; see, for example, Carrano et al. in *Proc. Nat'l. Acad. Sci. USA* 76: 1382–1384 (1979).

Next, an aqueous dispersion of the so isolated chromosomes has admixed therewith a crosslinking agent for the protein (i.e., histones and nonhistones) present in the chromosomal chromatin with the DNA. Conveniently, the crosslinking agent reacts with a polar group of one or more polar group containing amino acids present in such protein, such as, for example, asparate, aspargine, arginine, glutamate, glutamine, histidine, lysine, serine, tyrosine, and tryptophan. The sulfhydro group of cysteine can also sometimes crosslink. A suitable crosslinking agent and a suitable in situ hybridization procedure are taught, for example, in Van Engh U.S. Pat. No. 4,770,992 (1988).

A probe composition of the invention is admixed with the crosslinked and preferably denatured chromosomes.

A resulting mixture is preferably subjected to a separation procedure to isolate unhybridized residual probe composition. However, as those skilled in the art will appreciate, if the concentration of residual probe composition is sufficiently low so as not to interfere, or excessively interfere, with the particular flow cytometric analysis contemplated, then such separation procedure can be circumvented.

A suitable separation procedure can involve centrifuging. The resulting chromosome cake is resuspended in an aqueous medium. A convenient resuspended concentration is about $5 \times 10^6$ chromosomes/ml. Conveniently, the suspension water has dissolved therein a buffer salt.

A resulting suspension is subjected to flow cytometric analysis using, for example, a dual beam cytometer, for example, such as described in the aforecited references.

The results so measured can be used, for example, to identify chromosomes based upon the gross specimen morphology, or to correlate the presence of a specific chromosome stain with the presence of any chromosome material. The correlation is made to discriminate against the background which could be confused with the specific stain.

Another technique combining flow cytometric detection with in situ hybridization using a probe composition of this invention uses interphase nuclei in suspensions in the manner taught, for example by Trask, et al. in Hum Genet (1988) 78:251–259.

(4) Probe Mixtures

It is a feature and advantage of the probe compositions of this invention that they can be admixed with other probe compositions and the like without adversely affecting the chemical structure or the functional capacity thereof. Thus, even though mixed probe compositions incorporate complex DNA segment mixtures under hybridizing conditions, these individual segments only hybridize with complementary target DNA so that the desired specific chromosomal staining is achieved. For example, prior to the first procedural step above indicated, a probe composition of this invention, prepared as above described, can be admixed, if desired, with another probe composition which, for example, contains labeled segments that are hybridizable to specific targets present in predetermined chromosomes, or chromosome regions. Such other probe compositions should preferably be suitable for usage in in situ hybridization under comparable conditions of temperature, time, and the like (relative to a probe composition of this invention).

For example, such other probe composition can be a direct labeled or an indirect labeled probe composition such as (a) another direct labeled probe composition of this invention; (b) a probe composition labeled by nick translation of that probe composition's DNA with fluorophore-labeled nucleoside triphosphates as described in Wiegant et al. in *Nucleic Acids Research* 19: 3237–3241 (1991); (c) an indirect labeled probe composition prepared by incorporating biotin- or digoxygenin-containing deoxynucleotide triphosphates into probe DNA as described in a number of publications including Wiegant et al. (op. cited) and Bhatt et al. in *Nucleic Acids Research* 16: 3951–3961 (1988); and/or (d) the indirect labeled probe compositions which contain chemical groups that react in a post hybridization reaction with chemical groups on modified fluorophores to form a bond between hybridized probe and fluorophore label, as described by Hopman et al. in *Experimental Cell Research* 169: 357–368 (1987); and the like.

Such a resulting mixed probe composition can then be used in an in situ hybridization procedure in a slide mounted specimen. In this procedure, each chromosomal target present in a specimen is stained with its preselected probe composition, to the extent, that such target is present in the specimen. Residual probes are subsequently separated from the resulting specimen in the same washing procedure.

Another feature and advantage of the probe compositions of this invention is that they can also be used for successively accomplished specific staining of preselected chromosomes even after the completion of a preceding hybridization procedure, such as an in situ hybridization procedure wherein a particular different target is involved, or the like.

Probe compositions of this invention are generally compatible with other in situ hybridization reagents. However, in the case of two or more indirect labeled probes in combination, care must be taken that no components are present which will cross-react with each other when in admixture.

EMBODIMENTS

The present invention is further illustrated by reference to the following examples.

Microscopy was performed on either a Zeiss Axioskop, Axioplan, or Axiophot fluorescence microscope. Filter sets used for viewing specimens stained by in situ hybridization were obtained from either Carl Zeiss, Inc. (Thornwood, N.Y.) or Omega Optical, Inc. (Brattleboro, Vt.) as shown in Table V.

EXAMPLE 1

Isolation of Human Chromosome-Specific DNA Probes

Human chromosome-specific DNA was obtained as recombinant phage libraries from Lawrence Livermore National Laboratories, constructed as described in Van Dilla, M. A. et al. (Biotechnology 4: 537–552, 1986). Deposits of these libraries have been made to the Lawrence Livermore National Laboratories (LLNL). These libraries were amplified by growth on an *E. coli* host strain. The amplified phage were purified, their DNA was extracted, and this DNA was digested with the restriction enzyme Hind III. Insert DNA was purified away from the lambda vector DNA and cloned into the Hind III site of the plasmid vector pBS (Strategene, La Jolla, Calif.). The resulting plasmids were transformed into an *E. coli* strain, DH5α (Bethesda Research Libraries, Gaithersburg, Md.), thereby creating recombinant plasmid libraries containing human chromosomes specific insert DNA.

The phage libraries exemplified herein correspond to ATCC #57754 (Chromosome 1); ATCC #57745 (Chromosome 4); ATCC #57701 (Chromosome 6); ATCC #57702 (Chromosome 8) and ATCC #'s 57722 and 57755 (Chromosome 7). The libraries are stored as 1 ml aliquots of frozen cells. These vials have been used as the primary source for chromosomal DNA. Plasmid libraries from these phage libraries are used for fermentation.

Bacteria were grown by fermentation. The seed stock obtained from Lawrence Livermore National Laboratories was cultured at 37° C. for 24 hr. on 1.6% agar plates containing ampicillin (200 microgram/ml) and YT broth, which contains 8 grams per liter (g/l) of Bacco Tryptone (Difco), 5 g/l of Bacco Yeast Extract (Difco), 15 g/l of Bacto Agar (Difco), and 5 g/l of sodium chloride. The cultured cells were harvested with 4 ml of YT broth containing 16 g/l of Bacto Tryptone (Difco), 10 g/l of Bacto Yeast Extract (Difco) and 5 g/l of sodium chloride, and 4 ml of 20% glycerol was added to each harvest. The *E. coli* cell culture was quickly frozen in 0.5 ml aliquots by submerging the vials in liquid nitrogen and stored at −80° C. until use.

The fermenter inoculum was prepared in 350 ml by culturing the seed culture in a Casamino Acid medium which contains 13.2 g/l $Na_2HPO4-7H_2O$, 3.0 g/l $KH_2PO_4$, 0.05 g/l NaCl, 1.0 g/l $NH_4Cl$, 10.0 g/l Casamino Acids (Difco); 0.03 g/l $MgSO_4$, 0.004 g/l $CaCl_2-2H_2O$, 3.0 g/l glucose, 0.025 g/l Thiamine-HCl, 0.0054 g/l $FeCl_3$, 0.0004 g/l $ZnSO_4$, 0.0007 g/l $CoCl_2$, 0.0007 g/l $Na_2MoO_4$, 0.0008 g/l $CuSO_4$, 0.0002 g/l $H_2BO_3$, and 0.0005 g/l $MnSO_4$ in a 2 liter baffled shaker flask at pH 7 and 37° C. The 350 ml culture was used to inoculate 4.2 liter of fermentation media containing 1% glucose, 13.2 g/l $Na_2HPO4-7H_2O$, 3.0 g/l $KH_2PO_4$, 0.05 g/l NaCl, 1.0 g/l $NH_4Cl$, 10.0 g/l Casamino Acids (Difco), 0.03 g/l $MgSO_4$, 0.004 g/l $CaCl_2-2H_2O$, 0.025 g/l Thiamine-HCl, 0.0054 g/l $FeCl_3$, 0.0004 g/l $ZnSO_4$, 0.0007 g/l $CoCl_2$, 0.0007 g/l $Na_2MoO_4$, 0.0008 g/l $CuSO_4$, 0.0002 g/l $H_2BO_3$, and 0.0005 g/l $MnSO_4$.

Bacterial cells were harvested employing a membrane cell-concentrator and a high speed centrifuge immediately after completion of the fermentation. The fermented cell broth was concentrated from 5 liters to approximately 800 ml employing a 0.45 micron ($\mu$m) membrane filter (2 square feet). The cell concentrate was then centrifuged at 7,000×g for 10 minutes in a refrigerated centrifuge. The bacterial cell pellets were recovered after discarding the supernatant.

The amounts of all of the reagents used in the isolation of the DNA are calculated relative to the initial wet cell mass of the cell pellet (in grams). To determine the amounts required, a multiplication factor "M" is calculated, and then each reagent is added at M times a fixed amount of that component. The factor M for a given cell mass is determined by dividing the cell mass, in grams, by 13. Thus, to process 130 grams of cell mass, an M factor of 10 is applied to the fixed amount of each individual reagent.

Plasmid DNA was extracted from bacterial cell pellets. Cell pellets were resuspended in 40×M milliliters of a solution of 50 mM glucose (filter sterilized), 10 mM NaEDTA (pH 7.5–8.0), and 25 mM Tris-HCl (pH 8.0). The cells were lysed with vigorous swirling after the addition of 80×M milliliters of a solution of 0.2 M NaOH and 1% (w/v) SDS. After a few minutes the turbidity of this solution decreased, indicating lysis of the cells. To the cleared solution was added 60×M milliliters of a solution containing 55.5 ml of glacial acetic acid and 147.5 grams of potassium acetate per 500 ml. These solutions were mixed thoroughly, resulting in the production of a flocculent precipitate. The supernatant was removed from the flocculent precipitate and this supernatant was centrifuged for 15 minutes at 7000×g to remove residual precipitate.

Nucleic acid was precipitated from the supernatant with one volume of ethanol followed by centrifugation for 10 minutes at 7000×g, and the nucleic acid pellets were resuspended in a total of 7×M milliliters of a solution containing 50 mM Tris-HCl (pH 8.0), 100 mM sodium acetate. The nucleic acid was then extracted with 1/2 volume of neutralized phenol and 1/2 volume of chloroform and precipitated with two volumes of ethanol. The nucleic acid was resuspended in 4×M milliliters of a solution containing 50 mM Tris-HCl (pH 8.0), 100 mM sodium acetate. A 10×M microliter portion of 10 mg/ml pancreatic Ribonuclease A solution (heat treated to inactivate DNase) was added to the resuspended nucleic acid solution. This mixture was allowed to digest for 30 minutes at room temperature or overnight at 4° C. An 8×M microliter portion of 20 mg/ml Proteinase K solution was then added and incubated at 55° C. for three hours. The DNA solution was then extracted with 1/2 volume of neutralized phenol and 1/2 volume of chloroform and precipitated with two volumes of ethanol. Precipitated DNA was collected by centrifugation for 15 minutes at 4500×g.

DNA was resuspended in 5.36×M milliliters of water, and then 0.64×M milliliters of 5 M NaCl and 2×M milliliters of 50% (w/v) polyethyleneglycol (PEG) (molecular weight 6000–8000) were added, incubated on ice water for one hour and precipitated by centrifugation for 15 minutes at 4500×g. The DNA was resuspended in 0.5×M milliliters of water and 1/10 volume of 3M sodium acetate and extracted with 1/2 volume of neutralized phenol and 1/2 volume of chloroform and precipitated with two volumes of ethanol. Precipitated DNA was collected by centrifugation for 15 minutes at 4500×g and dried under vacuum. The purified DNA was resuspended in 0.6×M milliliters of deionized water. The DNA concentration was determined by fluorometry.

Finally, the purified DNA was disrupted into small fragments of approximately 300 base pairs by sonication using a Branson Sonifier 450 (Danbury, Conn.). This size of fragments has been empirically determined to be the optimum for DNA probes used for in situ hybridization. Four milligrams of the purified plasmid DNA prepared above was resuspended in 2 ml of water and immersed in a dry ice/ethanol bath to prevent boiling during sonication. The microtip of the sonication device was immersed in this solution until the tip was 2–5 mm from the bottom of the tube. Sonication was carried out at an output power of 25–30 watts, discontinuously, with an 80% duty cycle(on 80% of time, off 20% of time), for a period of 5 minutes. Following sonication, the DNA was precipitated by the addition of 0.2 ml of 3 M sodium acetate (pH 5.5) and 4 ml of ethanol. The precipitate was recovered by centrifugation for 5 minutes at 8,000×g and vacuum dried.

EXAMPLE 2

Bisulfite Catalyzed Transamination of Probe Precursor DNA

Probe precursor DNA was transaminated by the addition of ethylenediamine to the C4 carbon atom of the base cytosine. This reaction is catalyzed by sodium bisulfite. Different probe DNA precursor DNA sets were transaminated. Thus, approximately 4 to 24% of the available deoxycytidine nucleotide sites are aminated for fluorescent labeling.

To prepare the bisulfite buffer, 1.7 ml of concentrated HCl was slowly added to 1 ml deionized $H_2O$ on ice. 1 ml fresh ethylenediamine (Sigma cat. #E-4379) was then slowly added on ice. After dissolution of the ethylenediamine, the solution was warmed to room temperature and 0.475 sodium metabisulfite (Aldrich Cat. #25,555-6) or sodium bisulfite (EM Science Cat. #SX0345-1) was added. Concentrated HCl was then slowly added to the bisulfite mixture until the pH reached 7.0, and the volume of the solution was adjusted to 5.0 ml.

To transaminated probe precursor DNA, 1 milligram of sonicated DNA was resuspended in 0.3 ml $H_2O$. The DNA was denatured by boiling at 100° C. for 5 minutes then quickly chilled in an ice water bath. The transamination reaction was initiated by the addition of 0.3 ml of this DNA solution to 2.7 ml of bisulfite buffer, and the reaction was incubated at either 25 or 37° C. for several hours to several days to achieve the desired degree of amination (see table below). The DNA solution was desalted by routine dialysis against 5–10 mM sodium borate (pH 8.0). After dialysis, 0.3 ml of 3 M sodium acetate (pH 5.5) was added to the dialysate. The aminated DNA was precipitated with 2.5 volumes of ethanol and recovered after centrifugation at 8,000×g for 10 minutes. The pellets were vacuum dried and rehydrated at a concentration of 3 mg/ml DNA. This solution was stored at −20° C. until use.

The extent of transamination of dC was determined by enzymatic digestion of the aminated DNA followed by separation of the resulting nucleosides on an FPLC chromatography system (Pharmacia LKB, Piscataway, N.J.). 5–10 μg of aminated DNA was diluted with water to 50 μl and the DNA purified on a spin column containing Sephadex C-25 (5Prime→3 Prime, Inc. Paoli, Pa.). The DNA was then dried, resuspended in 12.0 μl $H_2O$, and 12.5 μl of 2×DNase 1 buffer (20 mM Tris, 10 mM $MgCl_2$, pH 7.5) and 0.5 μl of deoxyribonuclease 1 (DNase 1) (BRL, 2 mg/474 μl, >10.000 U/mg) was added to the DNA and the solution incubated in a 37° C. water bath for 1 hr. 50 μl of 2×PD1/alk. phos. buffer (100 mM Tris, 200 mM NaCl, 28 mM $MgCl_2$, 2 mM $ZnCl_2$, pH 9.0), 19 μl of water, 5.0 μl of phosphodiesterase 1 (PD1) (Pharmacia LKB, 1,000 U/ml dissolved in 1×PD1/alk. phos. buffer), and 1.0 μl calf intestinal alkaline phosphatase (Promega, 10,000 U/ml) was then added and the solution incubated for an additional 2 hr at 37° C. The digested sample was then applied to a MinoRPC column (Pharmacia LKB) and a linear gradient between buffer A (97.5:2.5 ion-pairing buffer:methanol, ion-pairing buffer—50 mM $KH_2PO_4$, 0.05% hexanesulfonic acid, pH 7.0) and buffer B (50:50 ion-pairing buffer:methanol) was used to elute the sample (a 0.8% increase in buffer B/min at a flow rate of 0.37 ml/min until 40% buffer B was reached, followed by a 3% increase in buffer B/min to 100% buffer B at a flow rate of 0.3 ml/min) while recording the DNA elution profile by absorbance. Each of the 4 natural deoxynucleosides and the transamination product of deoxycytidine eluted separately and the amount of deoxycytidine transaminated was determined from the relative areas under the deoxycytidine and transaminated deoxycytidine peaks in the elution profile. Typical results are listed below for two preparations of sonicated plasmid DNA containing sequences from human chromosome #4.

TABLE VI

| Transmission Reaction Conditions | | | |
|---|---|---|---|
| DNA Preparation | Temp. (° C.) | Time | % dC Aminated |
| 1 | 37 | 2 day | 22 |
| 2 | 37 | 63 hr | 19 |
| 2 | 37 | 38 hr | 19 |
| 2 | 37 | 15 hr | 13 |
| 2 | 25 | 63 hr | 12 |
| 2 | 25 | 38 hr | 10 |
| 2 | 25 | 15 hr | 4.6 |

EXAMPLE 3

Labeling of Transaminated Chromosome-Specific Probe Precursor DNA with the Fluorophore 7-Amino-4-methylcoumarin-3-acetic Acid, Succinimidyl Ester (AMCA)

Transaminated probe precursor DNA (average length 300 bp, 20% of deoxycytosine aminated) specific to human chromosome 1 were conjugated with 7-amino-4-methylcoumarin-3-acetic acid, succinimidyl ester (AMCA). Sixty micrograms of transaminated DNA were dried and then resuspended in 673 microliters of 200 mM 3-[N-morpholino] propane sulfonic acid (MOPS) as a buffer at pH 7.4. Twenty-six and eight tenths microliters of a 50 mM solution of AMCA in dimethyl sulfoxide (a 150 fold molar excess) was added to the suspension of transaminated DNA.

This reaction proceeded with stirring in darkness at room temperature for approximately 18 hours. The excess fluorophore was separated from the labeled DNA by passing the reaction over a Sephadex C-25 column chat was 28 cm high with an internal diameter of 1 cm. The desired fraction (the column void volume) was eluted with water and dried to reduce the total volume. Two ethanol precipitations of the labeled DNA completed the purification to provide the AMCA probe. An absorbance spectrum showed that 4.8% of the bases were labeled. In subsequent preparations one of the ethanol precipitation steps was performed first, followed by the column purification step, and the second ethanol precipitation step was performed last. Both purification procedures provided good results.

This embodiment of the invention was tested by in situ hybridization using conventional methods for the preparation of chromosome spreads. The target DNA consisted of cultured normal white blood cells that were treated to arrest the cells in metaphase. These cells were dropped onto a glass microscope slide from a distance of about 3 feet to break open the nuclei. Before hybridizing the slide was placed for 2 minutes in a denaturing solution of 70% formamide/0.3 M NaCl/30 mM sodium citrate (pH 7) at 70° C. The slide was then dehydrated by passing through 70%, 85% and 100% ethanol baths (2 minutes each).

The hybridization mix that was placed on each slide (10 μl) was 50% formamide/10% dextran sulfate/0.3 M NaCl/30 mM sodium citrate (pH 7)/0.5 μg sonicated salmon sperm DNA (used as carrier). The concentrations of blocking DNA (Cot1 DNA or sonicated human placental DNA) and of probe added to the basic mix were varied. Ten microliters of the complete hybridization mixture were denatured by heating to 70° C. for 5 minutes and then allowed to hybridize at 37° C. for one hour. The mix was applied directly to the slide, covered with a glass coverslip, and allowed to hybridize overnight at 37° C. in a humidified chamber.

The next day the excess probe was removed by washing the slide three times, 15 minutes each, at 45° C. in 50% formamide/0.3 M NaCl/30 mM sodium citrate (pH 7), then washing the slide in 0.3 M NaCl/30 mM sodium citrate (pH 7) for 15 minutes at 45° C., followed by washing the slide in 0.1 M sodium phosphate (pH 7)/0.1% NP40 detergent (NP40 is octylphenoxypolyethoxyethanol, which is a nonionic surfactant sold by Calbiochem, La Jolla, Calif.) for 15 minutes at 45° C. Finally the slide was washed twice, for two minutes each, in 0.1 M sodium phosphate (pH 7)/0.1% NP40 detergent at room temperature and the slide air dried. 7.5 μl of antifade solution, used to reduce the rate of fluorophore photo-oxidation, was applied directly to the slide and a coverslip placed over the drop of antifade solution. The antifade solution is described in J. Immuno. Methods 43: 349 (1981) and is made as follows: 100 milligrams of p-phenylenediamine dihydrochloride is dissolved in 10 milliliters of phosphate buffered saline solution. The pH of this solution is adjusted to pH 8 with a bicarbonate buffer solution prepared by adding 0.42 g NaHCO$_3$ to 10 milliliters of water then adjusting the pH to 9.0 by the addition of 50% (w/v) NaOH. The pH adjusted solution of p-phenylenediamine dihydrochloride is added to 90 milliliters of glycerol and the resulting solution is filtered through a 0.22 μm filtration device. This solution is stored in the dark at −20° C. The antifade solution optionally contained 0.2 μg propidium iodide/ml as a general chromosome stain to permit the visualization of all chromosomes. The slide was then viewed with a fluorescence microscope using filter set #1 or #2 for the AMCA and set #10 for the propidium iodide.

TABLE VII

Qualitative Results:

| [AMCA Probe] (ng/10 μl) | [Blocking DNA]; P = placental, C = Cot1 (μg/10 μl) | Visual Description slide under microscope 40–100%) | |
|---|---|---|---|
| | | Specificity | Intensity |
| 100 | 2.25P | | − |
| 316 | 2.25P | +++ | + |
| 500 | 2.25P | +++ | ++ |
| 1,000 | 2.25P | +++ | ++ |
| 1,000 | 6.75P | +++ | +++ |
| 100 | 1.3C | +/− | +/− |
| 316 | 1.3C | +++ | ++ |
| 1,000 | 1.3C | ++ | +++ |

Code:
Specificity: (−) none apparent, (+) small amount of specificity, (++) reasonable specificity, (+++) good specificity
Intensity: (−) not visible, (+) barely visible, (++) fairly visible, (+++) bright, (++++) very bright AMCA-labeled probes show good specificity with either placental or Cot1DNA. Higher probe concentrations are preferable for observing good fluorescence intensity.

It was often found that adding 6.75 μg rather than 2.25 μg of human placental DNA resulted in improved specificity and/or intensity of probes to whole chromosomes.

EXAMPLE 4

Labeling of Transaminated Chromosome-Specific Probe Precursor DNA with the Fluorophore Texas Red Sulfonyl Chloride (TxRd)

Two different transaminated probe precursor DNAs (average length 300 bp, one to 20%, the other to 4.6% of deoxycytosines aminated) specific to human chromosome 7 were conjugated with Texas Red Sulfonyl chloride (TxRd). Forty micrograms of each such transaminated DNA were dried and then resuspended in 270 microliters of 50 mM sodium borate, pH 9.3. Thirty microliters of a 30 mM solution of TxRd in N,N-dimethylformamide (a 150-fold molar excess) was added to the suspensions of transaminated DNA. These reactions proceeded with stirring in darkness at room temperature overnight (approximately 18 hours). The excess fluorophore was separated from the labeled DNAs by precipitating the DNAs from ethanol. The precipitated materials were resuspended in water and each passed over a Sephadex G-25 column that was 28 cm high with an internal diameter of 1 cm. The desired fractions (the column void volumes) were eluted with water and dried to reduce the total volumes. A second ethanol precipitation of the labeled DNAs completed the purification. Absorbance spectra of the labeled products showed that 3.2% of the total nucleotides in the 5% (total nucleotides) aminated DNA preparation were labeled and that 1.0% of the total nucleotides in the 1.2% (total nucleotides) aminated DNA preparation were labeled. This procedure provides a TxRd probe.

This embodiment of the invention was tested by in situ hybridization using conventional methods for the preparation of chromosome metaphase spreads. The target DNA consisted of cultured normal white blood cells that were treated to arrest the cells in metaphase. These cells were dropped onto a glass microscope slide from about three feet to break open the nuclei and expose the chromosomes. Before hybridizing the slide was placed for 2 minutes in a denaturing solution of 70% formamide/0.3 H NaCl/30 mM sodium citrate (pH 7) at 70° C. The slide was then dehydrated by passing through 70%, 85% and 100% ethanol baths (2 minutes each).

The hybridization mix that was placed on slides (10 μl) was here always 50% formamide/10% dextran sulfate/0.3 M NaCl/30 mM sodium citrate (pH 7)/0.5 μg sonicated salmon sperm DNA (used as carrier). The concentrations of blocking DNA (Cot1 DNA or sonicated human placental DNA) and of probe added to the basic mix were varied. Ten microliters of the complete hybridization mixture were denatured by hearing to 70° C. for 5 minutes and then allowed to hybridize au 37° C. for one hour. The mix was applied directly to the slide, covered with a glass coverslip, and allowed to hybridize overnight at 37° C. in a humidified chamber.

The next day the excess probe was removed by washing the slide three times, 15 minutes each, at 45° C. in 50% formamide/0.3 M NaCl/30 mM sodium citrate (ph 7), then washing the slide in 0.3 M NaCl/30 mM sodium citrate (pH 7) for 15 minutes at 45° C., followed by washing the slide in 0.1 M sodium phosphate (pH 7)/0.1% NP40 detergent (NP40 is octylphenoxypolyethoxyethanol, which is a non-ionic surfactant sold by Calbiochem, La Jolla, Calif.) for 15 minutes at 45° C. Finally the slide was washed twice, for two minutes each, in 0.1 M sodium phosphate (pH 7)/0.1% NP40 detergent at room temperature and the slide air dried. 7.5 μl of antifade solution, used to reduce the rate of fluorophore photo-oxidation, was applied directly to the slide and a coverslip placed over the drop of antifade solution. (See Example 3). The antifade solution optionally contained 1.0 μg 4,6-diamidino-2-phenylindole hydrochloride (DAPI)/ml general chromosome stain to permit the visualization of all chromosomes. The slide was then viewed with a fluorescence microscope using filter set #9 for Tx Rd and set #1 or #2 for DAPI.

TABLE VIII

Qualitative Results:

| [TxRd Probe] (ng/10 μl) | [Blocking DNA]; P = placental, C = Cot1 (μg/10 μl) | Visual Description (slide under microscope 40–100%) | |
|---|---|---|---|
| | | Specificity | Intensity |
| 5% aminated, 3% Tx Rd-labeled (based upon total nucleotides) probe: | | | |
| 32 | 2.25P | + | ++ |
| 100 | 2.25P | + | ++ |
| 316 | 2.25P | − | +++ |
| 1,000 | 2.25P | − | ++++ |
| 100 | 6.75P | − | ++ |
| 316 | 6.75P | ++ | +++ |
| 1,000 | 6.75P | − | ++++ |
| 100 | 1.3C | ++ | ++ |
| 316 | 1.3C | ++ | +++ |
| 1,000 | 1.3C | ++ | ++++ |
| 1.2% aminated, 1% Tx Rd-labeled (based upon total nucleotides) probe: | | | |
| 100 | 1.3C | ++++ | +++/++++ |
| 316 | 1.3C | ++++ | ++++ |

Code:
Specificity: (−) none apparent, (+) small amount of specificity, (++) reasonable specificity, (+++) good specificity, (++++) very good specificity.
Intensity: (−) not visible, (+) barely visible, (++) fairly visible, (+++) bright, (++++) very bright.

The data show that Tx Rd-labeled probes perform better when labeled to a lower degree. Specificity was much improved when the degree of amination was reduced from 20% to 4.6% of the deoxycytosines. Even low probe concentrations (100 ng/10 μl) provided very good results when using the 1% labeled probe.

EXAMPLE 5

Labeling of Transaminated Chromosome-Specific Probe Precursor DNA with the Fluorophore 5-(and-6)-carboxy-X-rhodamine, Succinimidyl Ester (CXR)

Two different transaminated probe precursor DNAs (average length 300 bp, one to 20%, the other to 4.6% of deoxycytosines aminated) specific to human chromosome 4 were conjugated with 5-(and-6)-carboxy-X-rhodamine, succinimidyl ester (CXR). Thirty-five micrograms of each such transaminated DNA were dried and then resuspended in 368 microliters of 200 mM MOPS, pH 7.4. Thirty-one and eight tenths microliters of a 25 mM solution of CXR in N,N-dimethylformamide (a 150-fold molar excess) was added to each suspension of transaminated DNA. These reactions proceeded with stirring in darkness at room temperature overnight (approximately 18 hours). The excess fluorophore was separated by precipitating the labeled DNAs from ethanol. The precipitated materials were resuspended in water and each passed over a Sephadex G-25 column that was 28 cm high with an internal diameter of 1 cm. The desired fractions (the column void volumes) were eluted with water and dried to reduce the total volumes. A second ethanol precipitation of the labeled DNAs completed the purification. Absorbance spectra of the labeled products showed that 4.9% of the total nucleotides in the 5% (total nucleotides) aminated DNA preparation were labeled and that 1.5% of the total nucleotides in the 1.2% (total nucleotides) aminated DNA preparation were labeled.

This embodiment of the invention was tested by in situ hybridization using conventional methods for the preparation of chromosome metaphase spreads. The target DNA consisted of cultured normal white blood cells that were treated to arrest the cells in metaphase. These cells were dropped onto a glass microscope slide from a distance of about 3 feet to break open the nuclei. Before hybridizing the slide was placed for 2 minutes in a denaturing solution of 70% formamide/0.3 M NaCl/30 mM sodium citrate (pH 7) at 70° C. The slide was then dehydrated by passing through 70%, 85% and 100% ethanol baths (2 minutes each).

The hybridization mix that was placed on slides (10 μl) was here always 50% formamide/10% dextran sulfate/0.3 M NaCl/30 mM sodium citrate (pH 7)/0.5 μg sonicated salmon sperm DNA (used as carrier). The concentrations of blocking DNA (Cot1 DNA or sonicated human placental DNA) and of probe added to the basic mix were varied. Ten microliters of the complete hybridization mixture were denatured by hearing to 70° C. for 5 minutes and then allowed to hybridize at 37° C. for one hour. The mix was applied directly to the slide, covered with a glass coverslip, and allowed to hybridize overnight at 37° C. in a humidified chamber.

The next day the excess probe was removed by washing the slide three times, 15 minutes each, at 45° C. in 50% formamide/0.3 M NaCl/30 mM sodium citrate (pH 7), then washing the slide in 0.3 M NaCl/30 mM sodium citrate (pH 7) for 15 minutes at 45° C., followed by washing the slide in 0.1 M sodium phosphate (pH 7)/0.1% NP40 detergent (NP40 is octylphenoxypolyethoxyethanol, which is a non-ionic surfactant sold by Calbiochem, La Jolla, Calif.) for 15 minutes at 45° C. Finally the slide was washed twice, for two minutes each, in 0.1 M sodium phosphate (pH 7)/0.1% NP40 detergent at room temperature and the slide air dried. 7.5 μl of antifade solution, used to reduce the race of fluorophore photo-oxidation, was applied directly to the slide and a coverslip placed over the drop of antifade solution. (See Example 3). The antifade solution optionally contained 1.0 µg 4,6-diamidino-2-phenylindole hydrochloride (DAPI)/ml as a general chromosome stain to permit the visualization of all chromosomes. The slide was then viewed with a fluorescence microscope using filter set #9 for CXR and set #1 or #2 for DAPI.

TABLE IX

Qualitative results:

| [CXR-Probe] | [Blocking DNA]; P = placental, | Visual Description (slide under microscope 40–100%) | |
|---|---|---|---|
| (ng/10 µl) | C = Cot1 (µg/10 µl) | Specificity | Intensity |
| 5% aminated, 4.9% CXR-labeled (based upon total nucleotides) probe: | | | |
| 100 | 1.3C | – | + |
| 316 | 1.3C | +++ | +++ |
| 1,000 | 1.3C | ++ | +++ |
| 1.2% aminated, 1.5% CXR-labeled (based upon total nucleotides) probe: | | | |
| 100 | 1.3C | ++++ | +++ |
| 316 | 1.3C | ++++ | +++ |
| 1,000 | 1.3C | +++ | ++++ |

Code:
Specificity: (–) none apparent, (+) small amount of specificity, (++) reasonable specificity, (+++) good specificity, (++++) very good specificity.
Intensity: (–) not visible, (+) barely visible, (++) fairly visible, (+++) bright, (++++) very bright.

The data show that CXR-labeled probes perform better when labeled to a lower degree. Specificity was improved when the degree of amination was reduced from 20% to 4.6% of the deoxycytosines. Even low probe concentrations (100 ng/10 µl) provided good results when using the 1.5% (total nucleotides) labeled probe.

EXAMPLE 6

Labeling of Transaminated Chromosome-Specific Probe Precursor DNA with the Fluorophore Lissamine Rhodamine B Sulfonyl Chloride (LisR)

Transaminated probe precursor DNA (average length 300 bp, 20% of deoxycytosines aminated) specific to human chromosome 4 were conjugated with lissamine rhodamine B sulfonyl chloride (LisR). Thirty micrograms of transaminated DNA were dried and then resuspended in 373 microliters of 50 mM sodium borate, pH 9.3. Twenty-seven and three tenths microliters of a 25 mM solution of LisR in N,N-dimethylformamide (a 150-fold molar excess) was added to the suspension of transaminated DNA. This reaction proceeded with stirring in darkness at room temperature overnight (approximately 18 hours). The excess fluorophore was separated from the labeled DNA first by an ethanol precipitation. The precipitated material was resuspended in water and passed over a Sephadex C-25 column that was 28 cm high with an internal diameter of 1 cm. The desired fraction (the column void volume) was eluted with water and dried to reduce the total volume. A second ethanol precipitation of the labeled DNA completed the purification. An absorbance spectrum showed that 3.8% of the bases were labeled. This procedure provides the LisR probe.

This embodiment of the invention was tested by in situ hybridization using conventional methods for the preparation of chromosome metaphase spreads. The target DNA consisted of cultured normal white blood cells that were created to arrest the cells in metaphase. These cells were dropped onto a glass microscope slide from about 3 feet to break open the nuclei. Before hybridizing the slide was placed for 2 minutes in a denaturing solution of 70% formamide/0.3 M NaCl/30 mM sodium citrate (pH 7) at 70° C. The slide was then dehydrated by passing through 70%, 85% and 100% ethanol baths (2 minutes each).

The hybridization mix that was placed on slides (10 µl) was here always 50% formamide/10% dextran sulfate/0.3 M NaCl/30 mM sodium citrate (pH 7)/0.5 µg sonicated salmon sperm DNA (used as carrier). The concentrations of blocking DNA (Cot1 DNA or sonicated human placental DNA) and of probe added to the basic mix were varied. Ten microliters of the complete hybridization mixture were denatured by heating to 70° C. for 5 minutes and then allowed to hybridize at 37° C. for one hour. The mix was applied directly to the slide, covered with a glass coverslip, and allowed to hybridize overnight at 37° C. in a humidified chamber.

The next day the excess probe was removed by washing the slide three times, 15 minutes each, at 45° C. in 50% formamide/0.3 M NaCl/30 mM sodium citrate (pH 7), then washing the slide in 0.3 M NaCl/30 mM sodium citrate (pH 7) for 15 minutes at 45° C., followed by washing the slide in 0.1 M sodium phosphate (pH 7)/0.1% NP40 detergent (NP40 is octylphenoxypolyethoxyethanol1, which is a nonionic surfactant sold by Calbiochem, La Jolla, Calif.) for 15 minutes at 45° C. Finally the slide was washed twice, for two minutes each, in 0.1 M sodium phosphate (pH 7)/0.1% NP40 detergent at room temperature and the slide air dried. 7.5 µl of antifade solution, used to reduce the rate of fluorophore photo-oxidation, was applied directly to the slide and a coverslip placed over the drop of antifade solution. (See Example 3). The antifade solution optionally contained 1.0 µg 4,6-diamidino-2-phenylindole hydrochloride (DAPI)/ml as a general chromosome stain to permit the visualization of all chromosomes. The slide was then viewed with a fluorescence microscope using filter set #7, #8, or #9 for LisR and set #1 or #2 for DAPI.

TABLE X

Qualitative Results:

| [LisR Probe] | [Blocking DNA]; P = placental, | Visual Description (slide under microscope 40–100%) | |
|---|---|---|---|
| (ng/10 µl) | C = Cot1 (µg/10 µl) | Specificity | Intensity |
| 100 | 2.25P | – | + |
| 316 | 2.25P | + | ++ |
| 1,000 | 2.25P | + | ++ |
| 100 | 6.75P | – | + |
| 316 | 6.75P | + | ++ |
| 1,000 | 6.75P | + | ++ |
| 100 | 1.3C | + | ++ |
| 316 | 1.3C | – | +++ |
| 1,000 | 1.3C | – | ++++ |

Code:
Specificity: (–) none apparent, (+) small amount of specificity, (++) reasonable specificity, (+++) good specificity
Intensity: (–) not visible, (+) barely visible, (++) fairly visible, (+++) bright, (++++) very bright.

LisR-labeled probes provide some specificity and good intensity relatively high degree of 5% labeling (total nucleotides).

EXAMPLE 7

Labeling of Transaminated Chromosome-Specific Probe Precursor DNA with the Fluorophore 5-(and-6)-Carboxytetramethylrhodamine, Succinimidyl Ester (CTMR)

Two different transaminated probe precursor DNAs (average length 300 bp, one to 20%, the other to 4.6% of deoxycytosines aminated) specific to human chromosome 4 were conjugated with 5-(and-6)-carboxytetramethyl-rhodamine, succinimidyl ester (CTMR). Fifty micrograms of each such transaminated DNA were dried and then resuspended in 377 microliters of 200 mM MOPS, pH 7.4. Twenty-two and eight tenths microliters of a 50 mM solution of CTMR in N,N-dimethylformamide (a 150-fold molar excess) was added to each transaminated DNA. These reactions proceeded with stirring in darkness at room temperature overnight (approximately 18 hours). The excess fluorophore was separated from the labeled DNAs first by an ethanol precipitation. The precipitated materials were resuspended in water and passed over a Sephadex G-25 column that was 28 cm high with an internal diameter of 1 cm. The desired fractions (the column void volumes) were eluted with water and dried to reduce the total volumes. A second ethanol precipitation of the labeled DNAs completed the purification. Absorbance spectra of the labeled products showed that 5.5% of the total nucleotides in the 5% (total nucleotides) aminated DNA preparation were labeled. This procedure provides the CTMR probe.

This embodiment of the invention was tested by in situ hybridization using conventional methods for the preparation of chromosome metaphase spreads. The target DNA consisted of cultured normal white blood cells that were created to arrest the cells in metaphase. These cells were dropped onto a glass microscope slide from about three feet to break open the nuclei, Before hybridizing the slide was placed for 2 minutes in a denaturing solution of 70% formamide/0.3 M NaCl/30 mM sodium citrate (pH 7) at 70° C. The slide was then dehydrated by passing through 70%, 85%, and 100% ethanol baths (2 minutes each).

The hybridization mix that was placed on slides (10 μl) was here always 50% formamide/10% dextran sulfate/0.3 M NaCl/30 mM sodium citrate (pH 7)/0.5μg sonicated salmon sperm DNA (used as carrier). The concentrations of blocking DNA (Cot1 DNA or sonicated human placental DNA) and of probe added to the basic mix were varied. Ten microliters of the complete hybridization mixture were denatured by heating to 70° C. for 5 minutes then allowed to hybridize at 37° C. for one hour. The mix was applied directly to the slide, covered with a glass coverslip, and allowed to hybridize overnight at 37° C. in a humidified chamber.

The next day the excess probe was removed by washing the slide three times, 15 minutes each, at 45° C. in 50% formamide/0.3 M NaCl/30 sodium citrate (pH 7), then washing the slide in 0.3 M NaCl/30 mM sodium citrate (pH 7) for 15 minutes at 45° C., followed by washing the slide in 0.1 M sodium phosphate (pH 7)/0.1% NP40 detergent (NP40 is octylphenoxypolyethoxyethanol, which is a non-ionic surfactant sold by Calbiochem, La Jolla, Calif.) for 15 minutes at 45° C. Finally the slide was washed twice, for two minutes each, in 0.1 M sodium phosphate (pH 7)/0.1% NP40 detergent at room temperature and the slide air dried. 7.5 μl of antifade solution, used to reduce the rate of fluorophore photo-oxidation, was applied directly to the slide and a coverslip placed over the drop of antifade solution. (See Example 3). The antifade solution optionally contained 1.0 μg 4,6-diamidino-2-phenylindole hydrochloride (DAPI)/ml as a general chromosome stain to permit the visualization of all chromosomes. The slide was then viewed with a fluorescence microscope using filter set #7 or #8 for CTMR and set #1 or #2 for DAPI.

Qualitative Results for 5% aminated, 5.5% CTMR-labeled (based upon total nucleotides) probe:

TABLE XI

| [CTMR Probe] | [Blocking DNA]; P = placental, | Visual Description (slide under microscope 40–100%) | |
| --- | --- | --- | --- |
| (ng/10 μl) | C = Cot1 (μg/10 μl) | Specificity | Intensity |
| 316 | 2.25 P | ++ | +++ |
| 1,000 | 2.25 P | +++ | +++ |
| 316 | 6.75 P | +++ | ++ |
| 1,000 | 6.75 P | +++ | ++++ |
| 100 | 1.3 C | ++++ | +++ |
| 316 | 1.3 C | ++++ | ++++ |
| 1,000 | 1.3 C | ++++ | ++++ |
| 100 | 3.9 C | ++++ | ++++ |
| 316 | 3.9 C | ++++ | ++++ |
| 1,000 | 3.9 C | ++++ | ++++ |

Code:
Specificity: (−) none apparent, (+) small amount of specificity, (++) reasonable specificity, (+++) good specificity, (++++) very good specificity.
Intensity: (−) not visible, (+) barely visible, (++) fairly visible, (+++) bright, (++++) very bright CTMR-labeled probes provided very good specificity and intensity, even with the 5% labeled (total nucleotides) probe. A probe prepared from the 4.6% (based on deoxycytosines) aminated DNA similarly showed very good results.

EXAMPLE 8

Labeling of Transaminated Chromosome-Specific Probe Precursor DNA with the Fluorophore5-(and-6)-carboxyfluorescein, Succinimidyl Ester (CFl)

Transaminated probe precursor DNA (average length 300 bp, 20% of deoxycytosines aminated) specific to human chromosome 4 were conjugated with 5-(and-6)-carboxyfluorescein, succinimidyl ester (CFl). Fifty micrograms of transaminated DNA were dried and then resuspended in 377 microliters of 200 mM MOPS, pH 7.4. Twenty-two and eight tenths microliter of a 50 mM solution of CFl in N,N-dimethylformamide (a 150-fold molar excess) was added to the transaminated DNA. This reaction proceeded with stirring in darkness at room temperature overnight (approximately 18 hours). The excess fluorophore was separated from the labeled DNA first by an ethanol precipitation. The precipitated material was resuspended in water and passed over a Sephadex C-25 column that was 28 cm high with an internal diameter of 1 cm. The desired fraction (the column void volume) was eluted in water and dried to reduce the total volume. A second ethanol precipitation of the labeled DNA completed the purification. An absorbance spectrum showed that 1.6% of the bases were labeled. The procedure provides the CFl probe.

This embodiment of the invention was tested by in situ hybridization using conventional methods for the preparation of chromosome metaphase spreads. The target DNA consisted of cultured normal white blood cells that were treated to arrest the cells in metaphase. These cells were dropped onto a glass microscope slide from about three feet to break open the nuclei. Before hybridizing the slide was placed for 2 minutes in a denaturing solution of 70% formamide/0.3 M NaCl/30 mM sodium citrate (pH 7) at 70°

C. The slide was then dehydrated by passing through 70%, 85% and 100% ethanol baths (2 minutes each).

The hybridization mix that was placed on slides (10 µl) was here always 50% formamide/10% dextran sulfate/0.3 M NaCl/30 mM sodium citrate (pH 7)/0.5 µg sonicated salmon sperm DNA (used as carrier). The concentrations of blocking DNA (Cot1 DNA or sonicated human placental DNA) and of probe added to the basic mix were varied. Ten microliters of the completed hybridization mixture were denatured by heating to 70° C. for 5 minutes and then allowed to hybridize at 37° C. for one hour. The mix was applied directly to the slide, covered with a glass coverslip, and allowed to hybridize overnight at 37° C. in a humidified chamber.

The next day the excess probe was removed by washing the slide three times, 15 minutes each, at 45° C. in 50% formamide/0.3 M NaCl/30 mM sodium citrate (pH 7), then washing the slide in 0.3 H NaCl/30 mM sodium citrate (pH 7) for 15 minutes at 45° C., followed by washing the slide in 0.1 M sodium phosphate (pH 7)/0.1% NP40 detergent (NP40 is octylphenoxypolyethoxyethanol, which is a nonionic surfactant sold by Calbiochem, La Jolla, Calif.) for 15 minutes at 45° C. Finally the slide was washed twice, for two minutes each, in 0.1 M sodium phosphate (pH 7)/0.1% NP40 detergent at room temperature and the slide air dried. 7.5 µl of antifade solution, used to reduce the rate of fluorophore photo-oxidation, was applied directly to the slide and a coverslip placed over the drop of antifade solution. (See Example 3). The antifade solution optionally contained 1.0 µg 4,6-diamidino-2-phenylindole hydrochloride (DAPI)/ml as a general chromosome stain to permit the visualization of all chromosomes. The slide was then viewed with a fluorescence microscope using filter set #4, #5, #6, #14 for CFl and set #1 or #2 for DAPI.

TABLE XII

Qualitative Results

| [CFl Probe] | [Blocking DNA]; P = placental, | Visual Description (slide under microscope 40–100%) | |
|---|---|---|---|
| (ng/10 µl) | C = Cot1 (µg/10 µl) | Specificity | Intensity |
| 316 | 2.25P | + | ++ |
| 316 | 6.75P | − | +++ |
| 1,000 | 6.75P | − | ++++ |
| 100 | 1.3C | ++ | ++ |
| 316 | 1.3C | ++ | +++ |
| 1,000 | 1.3C | − | ++++ |
| 100 | 3.9C | + | +++ |
| 316 | 3.9C | + | +++ |
| 1,000 | 3.9C | ++ | +++ |
| 100* | 1.3C | +++ | +++ |
| 316* | 1.3C | ++ | +++ |
| 1,000* | 1.3C | − | ++ |

Code:
Specificity: (−) none apparent, (+) small amount of specificity, (++) reasonable specificity, (+++) good specificity
Intensity: (−) not visible, (+) barely visible, (++) fairly visible, (+++) bright, (++++) very bright
*No carrier DNA present.

CFl-labeled probes provided good intensity with sufficient levels of specificity.

EXAMPLE 9

Labeling of Transaminated Chromosome-Specific-Probe Precursor DNA with the Fluorophore Fluorescence-5-isothiocyanate (FITC)

Two different transaminated probe precursor DNAs (average length 300 bp, one to 20%, the other to 4.6% of deoxycytosines aminated) specific to human chromosome 7 were conjugated with fluorescein-5-isothiocyanate (FITC). Forty micrograms of each such transaminated DNA were dried and then resuspended in 244 microliters of 50 mM sodium borate, pH 9.3. Six and one tenth microliters of a 50 mM solution of FITC in N,N-dimethylformamide (a 50-fold molar excess) was added to the suspensions of transaminated DNA. These reactions proceeded with stirring in darkness at room temperature overnight (approximately 18 hours). The excess fluorophore was separated from the labeled DNAs first by an ethanol precipitation. The precipitated materials were resuspended in water and each passed over a Sephadex G-25 column that was 28 cm high with an internal diameter of 1 cm. The desired fractions (the column void volumes) were eluted with water and dried to reduce the total volumes. A second ethanol precipitation of the labeled DNAs completed the purification. Absorbance spectra of the labeled products showed that 2.2% of the total nucleotides in the 5% (total nucleotides) aminated DNA preparation were labeled and that 0.42% of the total nucleotides in the 1.2% (total nucleotides) aminated DNA preparation were labeled.

This embodiment of the invention was tested by in situ hybridization using conventional methods for the preparation of chromosome metaphase spreads. The target DNA consisted of cultured normal white blood cells that were created to arrest the cells in metaphase. These cells were dropped onto a glass microscope slide from about three feet to break open the nuclei. Before hybridizing the slide was placed for 2 minutes in a denaturing solution of 70% formamide/0.3 M NaCl/30 mM sodium citrate (pH 7) at 70° C. The slide was then dehydrated by passing through 70%, 85% and 100% ethanol baths (2 minutes each).

The hybridization mix that was placed on slides (10 µl) was here always 50% formamide/10% dextran sulfate/0.3 M NaCl/30 mM sodium citrate (pH 7)/0.5 µg sonicated salmon sperm DNA (used as carrier).

The concentrations of blocking DNA (Cot1 DNA or sonicated human placental DNA) and probe added to the basic mix were varied. Ten microliters of the complete hybridization mixture was denatured by heating to 70° C. for 5 minutes and then allowed to hybridize at 37° C. for one hour. The mix was applied directly to the slide, covered with a glass coverslip, and allowed to hybridize overnight at 37° C. in a humidified chamber.

The next day the excess probe was removed by washing the slide three times, 15 minutes each, at 45° C. in 50% formamide/0.3 M NaCl/30 mM sodium citrate (pH 7), then washing the slide in 0.3 M NaCl/30 mM sodium citrate (pH 7) for 15 minutes at 45° C., followed by washing the slide in 0.1 M sodium phosphate (pH 7)/0.1% NP40 detergent (NP40 is octylphenoxypolyethoxyethanol, which is a nonionic surfactant sold by Calbiochem, La Jolla, Calif.) for 15 minutes at 45° C. Finally the slide was washed twice, for two minutes each, in 0.1 M sodium phosphate (pH 7)/0.1% NP40 detergent at room temperature and the slide air dried. 7.5 µl of antifade solution, used to reduce the rate of fluorophore photo-oxidation, was applied directly to the slide and a coverslip placed over the drop of antifade solution. (See Example 3). The antifade solution optionally contained 1.0 µg 4,6-diamidino-2-phenylindole hydrochloride (DAPI)/ml as a general chromosome stain to permit the visualization of all chromosomes. The slide was then viewed with a fluorescence microscope using filter set #4, #5, #6 or #14 for FITC and set #1 or #2 for DAPI.

TABLE XIII

Qualitative Results

| [FITC Probe] | [Blocking DNA]; P = placental | Visual Description (slide under microscope 40–100%) | |
|---|---|---|---|
| (ng/10 µl) | C = Cot1 (µg/10 µl) | Specificity | Intensity |
| 5% aminated, 2.2% FITC-labeled (based on total nucleotides) probe: | | | |
| 32 | 2.25P | − | + |
| 102 | 2.25P | + | ++ |
| 323 | 2.25P | − | +++ |
| 32 | 6.75P | − | − |
| 100 | 6.75P | − | − |
| 316 | 6.75P | + | ++ |
| 1,000 | 6.75P | + | +++ |
| 100 | 1.3C | − | ++ |
| 316 | 1.3C | + | +++ |
| 1,000 | 1.3C | − | ++++ |
| 1.2% aminated, 0.42% FITC-labeled (based on total nucleotides) probe: | | | |
| 100 | 1.3C | ++++ | +++ |
| 316 | 1.3C | ++++ | ++++ |

Code:
Specificity: (−) none apparent, (+) small amount of specificity, (++) reasonable specificity, (+++) good specificity, (++++) very good specificity.
Intensity: (−) not visible, (+) barely visible, (++) fairly visible, (+++) bright, (++++) very bright FITC-labeled probes provide very good specificity and intensity when the degree of labeling is kept low. Specificity is poor when the degree of labeling is high.

EXAMPLE 10

Labeling of Transaminated Chromosome-Specific Probe Precursor DNA with the Fluorophore 7-Diethylaminocoumarin-3-carboxylic Acid, Succinimidyl Ester (DECCA)

Transaminated probe precursor DNA (average length 300 bp, 20% of deoxycytosines aminated) specific to human chromosome 4 were conjugated with 7-diethylaminocoumarin-3-carboxylic acid, succinimidyl ester (DECCA). Forty micrograms of transaminated DNA were dried and then resuspended in 364 microliters of 200 mM MOPS, pH 7.4. Thirty-six and four tenths microliters of a 25 mM solution of DECCA in N,N-dimethylformamide (a 150-fold molar excess) was added to the transaminated DNA. This reaction proceeded with stirring in darkness at room temperature overnight (approximately 18 hours). The excess fluorophore was separated from the labeled DNA first by an ethanol precipitation. The precipitated material was resuspended in water and passed over a Sephadex C-25 column that was 28 cm high with an internal diameter of 1 cm. The desired fraction (the column void volume) was eluted with water and dried to reduce the total volume. A second ethanol precipitation of the labeled DNA completed the purification. An absorbance spectrum showed that 1.9% of the bases were labeled. This procedure provides the DECCA probe.

This embodiment of the invention was tested by in situ hybridization using conventional methods for the preparation of chromosome metaphase spreads. The target DNA consisted of cultured normal white blood cells that were treated to arrest the cells in metaphase. These cells were dropped onto a glass microscope slide from about three feet to break open the nuclei. Before hybridizing the slide was placed for 2 minutes in a denaturing solution of 70% formamide/0.3 M NaCl/30 mM sodium citrate (pH 7) at 70° C. The slide was then dehydrated by passing through 70%, 85% and 100% ethanol baths (2 minutes each).

The hybridization mix that was placed on slides (10 µl) was here always 50% formamide/10% dextran sulfate/0.3 M NaCl/30 mM sodium citrate (pH 7)/0.5 µg sonicated salmon sperm DNA (used as carrier). The concentrations of blocking DNA (Cot1 DNA or sonicated human placental DNA) and of probe added to the basic mix were varied. Ten microliters of the complete hybridization mixture were denatured by heating to 70° C. for 5 minutes and then allowed to hybridize at 37° C. for one hour. The mix was applied directly to the slide, covered with a glass coverslip, and allowed to hybridize overnight at 37° C. in a humidified chamber.

The next day the excess probe was removed by washing the slide three times, 15 minutes each, at 45° C. in 50% formamide/0.3 M NaCl/30 mM sodium citrate (pH 7), then washing the slide in 0.3 M NaCl/30 mM sodium citrate (pH 7) for 15 minutes at 45° C., followed by washing the slide in 0.1 M sodium phosphate (pH 7)/0.1% NP40 detergent (NP40 is octylphenoxypolyethoxyethanol, which is a non-ionic surfactant sold by Calbiochem, La Jolla, Calif.) for 15 minutes at 45° C. Finally the slide was washed twice, for two minutes each, in 0.1 M sodium phosphate (pH 7)/0.1% NP40 detergent at room temperature and the slide air dried. 7.5 µl of antifade solution, used to reduce the race of fluorophore photo-oxidation, was applied directly to the slide and a coverslip placed over the drop of antifade solution. (See Example 3). The antifade solution optionally contained 0.2 µg propidium iodide/ml as a general chromosome stain to permit the visualization of all chromosomes. The slide was then viewed with a fluorescence microscope using filter set #3 for DECCA and set #10 for propidium iodide. Since the emission characteristics of filter set #3 are poorly matched to the emission maximum of DECCA, the observed intensities are therefore lower than expected for a filter set better matched to the spectral properties of DECCA such as filter set #13.

TABLE XIV

Qualitative Results

| [DECCA Probe] | [Blocking DNA]; P = placental, | Visual Description (slide under microscope 40–100%) | |
|---|---|---|---|
| (ng/10 µl) | C = Cot1 (µg/10 µl) | Specificity | Intensity |
| 316 | 2.25P | + | + |
| 1,000 | 2.25P | + | + |
| 100 | 1.3C | − | + |
| 316 | 1.3C | ++ | ++ |
| 1,000 | 1.3C | +++ | ++ |

Code:
Specificity: (−) none apparent, (+) small amount of specificity, (++) reasonable specificity, (+++) good specificity
Intensity: (−) not visible, (+) barely visible, (++) fairly visible (+++) bright, (++++) bright DECCA-labeled probes can provide good specificity, particularly when using Cot1 DNA, and reasonable intensity, even when using a relatively poorly adapted filter set such as set #3. When later viewed with filter set #13, equivalent specificity and higher intensity were observed.

EXAMPLE 11

Labeling of Transaminated Chromosome-Specific Probe Precursor DNA with the Fluorophore Tetramethylrhodamine-5-(and 6)-isothiocyanate (TRITC)

Transaminated probe precursor DNA average length 300 bp, 20% of deoxycytosines aminated) specific to human chromosome 7 were conjugated with tetramethylrhodamine-5-(and 6)-isothiocyanate (TRITC). Forty micrograms of transaminated DNA were dried and then resuspended in 244 microliters of 50 mM sodium borate, pH 9.3. Six and one tenth μl of a 50 mM solution of TRITC in dimethyl sulfoxide (a 50-fold excess) was added to the transaminated DNA. This reaction proceeded with stirring in darkness at room temperature overnight (approximately 18 hours). The excess fluorophore was separated from the labeled DNA first by an ethanol precipitation. The precipitated material was resuspended in water and passed over a Sephadex C-25 column that was 28 cm high with an internal diameter of 1 cm. The desired fraction (the column void volume) was eluted with water and dried to reduce the total volume. A second ethanol precipitation of the labeled DNA completed the purification. An absorbance spectrum showed that 3.4% of the bases were labeled.

This embodiment of the invention was tested by in situ hybridization using conventional methods for the preparation of chromosome metaphase spreads. The target DNA consisted of cultured normal white blood cells that were created to arrest the cells in metaphase. These cells were dropped onto a glass microscope slide from about three feet to break open the nuclei. Before hybridizing the slide was placed for 2 minutes in a denaturing solution of 70% formamide/0.3 M NaCl/30 mM sodium citrate (pH 7) at 70° C. The slide was then dehydrated by passing through 70%, 85%, and 100% ethanol baths (2 minutes each).

The hybridization mix that was placed on slides (10 μl) was here always 50% formamide/10% dextran sulfate/0.3 M NaCl/30 mM sodium citrate (pH 7)/0.5 μg sonicated salmon sperm DNA (used as a carrier). The concentrations of blocking DNA (Cot1 DNA or sonicated human placental DNA) and of probe added to the basic mix were varied. Ten microliters of the complete hybridization mixture were denatured by heating to 70° C. for 5 minutes and then allowed to hybridize at 37° C. for one hour. The mix was applied directly to the slide, covered with a glass coverslip, and allowed to hybridize overnight at 37° C. in a humidified chamber.

The next day the excess probe was removed by washing the slide three times, 15 minutes each, at 45° C. in 50% formamide/0.3 M NaCl/30 mM sodium citrate (pH 7), then washing the slide in 0.3 M NaCl/30 mM sodium citrate (pH 7) for 15 minutes at 45° C., followed by washing the slide in 0.1 M sodium phosphate (pH 7)/0.1% NP40 detergent (NP40 is octylphenoxypolyethoxyethanol, which is a non-ionic surfactant sold by Calbiochem, La Jolla, Calif.) for 15 minutes at 45° C. Finally the slide was washed twice, for two minutes each, in 0.1 M sodium phosphate (pH 7)/0.1% NP40 detergent at room temperature and the slide air dried. 7.5 μl of antifade solution, used to reduce the rate of fluorophore photo-oxidation, was applied directly to the slide and a coverslip placed over the drop of antifade solution. (See Example 3). The antifade solution optionally contained 1.0 μg 4,6-diamidino-2-phenylindole hydrochloride (DAPI)/ml as a general chromosome stain to permit the visualization of all chromosomes. The slide was then viewed with a fluorescence microscope using filter set #7 and #8 for TRITC and set #1 or #2 for DAPI.

TABLE XV

Qualitative Results

| [TRITC Probe] (ng/10 μl) | [Blocking DNA]; P = placental, C = Cot1 (μg/10 μl) | Visual Description slide under microscope 40–100%) | |
|---|---|---|---|
| | | Specificity | Intensity |
| 316 | 2.25P | −/+ | + |
| 95 | 2.25P | + | + |
| 300 | 2.25P | + | ++ |
| 32 | 6.75P | + | ++ |
| 100 | 6.75P | +++ | ++/+++ |
| 316 | 6.75P | +++ | +++ |
| 1,000 | 6.75P | ++/+++ | ++++ |
| 100 | 1.3C | +++ | +++ |
| 316 | 1.3C | ++ | +++ |
| 1,000 | 1.3C | + | ++++ |

Code:
Specificity: (−) none apparent, (+) small amount of specific (++) reasonable specificity, (+++) good specificity
Intensity: (−) not visible, (+) barely visible, (++) fairly visible, (+++) bright, (++++) very bright TRITC-labeled probes can provide both specificity and high intensity even when using the relatively highly labeled (5% of total nucleotides) probes.

EXAMPLE 12

Use of Multiple Fluorescently Labeled Reagents

The target DNA consisted of cultured normal white blood cells that were treated to arrest the cells in metaphase. These cells were dropped onto a glass microscope slide from about 3 feet to break open the nuclei. Before hybridizing the slide was placed for 2 minutes in a denaturing solution of 70% formamide/0.3 M NaCl/30 mM sodium citrate (pH 7) at 70° C. The slide was then dehydrated by passing through 70%, 85%, and 100% ethanol baths (2 minutes each).

The hybridization mix that was placed on each slide (10 μl) contained two to five fluorophore-labeled probes, specific for different chromosome pairs, and 50% formamide/10% dextran sulfate/0.3 M NaCl/30 nM sodium citrate (pH 7). In some experiments the mix contained 0.5 μg sonicated salmon sperm DNA (used as carrier). The concentrations of blocking DNA (Cot1 DNA or sonicated human placental DNA) added to the basic mix were varied. Ten microliters of the complete hybridization mixture were denatured by heating to 70° C. for 5 minutes and then allowed to hybridize at 37° C. for one hour. This mix was applied directly to the slide, covered with a glass coverslip, and allowed to hybridize overnight at 37° C. in a humidified chamber.

The next day the excess probes were removed by washing the slide three times, 15 minutes each, at 45° C. in 50% formamide/0.3 M NaCl/30 mM sodium citrate (pH 7), then washing the slide in 0.3 M NaCl/30 mM sodium citrate (pH 7) for 15 minutes at 45° C., followed by washing the slide in 0.1 M sodium phosphate (pH 7)/0.1% NP40 detergent (NP40 is octylphenoxypolyethoxyethanol, which is a non-ionic surfactant sold by Calbiochem, La Jolla, Calif.) for 15 minutes at 45° C. Finally the slide was washed twice, for two minutes each, in 0.1 M sodium phosphate (pH 7)/0.1% NP40 detergent at room temperature and the slide air dried. 7.5 μl of antifade solution, used to reduce the rate of fluorophore photo-oxidation, was applied directly co the slide and a coverslip placed over the drop of antifade solution. (See Example 3). The slide was then viewed with a fluorescence microscope using various filter sets to differentiate the emission from the several different fluorescent labels.

The combinations and concentrations of labeled probes used simultaneously in hybridizations are listed in the following table. Each combination of two, three, four, or five probes which was tested is listed together in the table without spacing. Some filter sets allowed only one fluorophore to be visualized while others allowed two fluorophores to be observed simultaneously. For example, the DECCA filter set (#3) allows the observation of both DECCA- and CF1-labeled probes. The DECCA- and CF1-stained chromosomes can be distinguished, though, because the CF1 filter set (#5, #6 or #14) allows visualization of only the CF1-stained chromosomes. This then identifies which of the two stained chromosome pairs results from fluorescein and which results from DECCA-labeled probes when viewed using the DECCA filter set #3. Likewise, the filters initially used were not able to distinguish tetramethylrhodamines from the rhodamine 101 derivatives, Texas Red and CXR, individually. However, using the TRITC filter set #8 the CTMR labels appear yellow-orange while the CXR and Texas Red labels appear more distinctly red allowing a visual distinction between the two different stains.

TABLE XVI

| PROBES Human Chromosome | Label | Conc. (ng/10 µl) | BLOCKER DNA P = placental DNA | CARRIER DNA C = Cotl DNA |
|---|---|---|---|---|
| 2 Probes, Simultaneous Hybridizations: | | | | |
| 4 | CTMR | 316 | 6.75P | 0.5 |
| 1 | AMCA | 1000 | | |
| 4 | CTMR | 316 | 13.5P | 0.5 |
| 1 | AMCA | 1000 | | |
| 3 Probes, Simultaneous Hybridizations: | | | | |
| 1 | CTMR | 316 | 1.3C | 0.5 |
| 4 | AMCA | 316 | | |
| 8 | DECCA | 316 | | |
| 1 | CTMR | 316 | 3.9C | 0.5 |
| 4 | AMCA | 316 | | |
| 8 | DECCA | 316 | | |
| 4 Probes, Simultaneous Hybridizations: | | | | |
| 1 | CTMR | 316 | 1.3C | 0 |
| 4 | AMCA | 316 | | |
| 7 | CXR | 316 | | |
| 8 | DECCA | 316 | | |
| 1 | CTMR | 316 | 1.3C | 0 |
| 4 | CFl | 316 | | |
| 6 | AMCA | 1000 | | |
| 8 | DECCA | 316 | | |
| 1 | AMCA | 316 | 1.3C | 0 |
| 4 | CXR | 316 | | |
| 6 | CTMR | 316 | | |
| 8 | DECCA | 316 | | |
| 1 | CTMR | 316 | 1.3C | 0 |
| 4 | CXR | 316 | | |
| 6 | AMCA | 1000 | | |
| 8 | DECCA | 316 | | |
| 5 Probes, Simultaneous Hybridizations: | | | | |
| 1 | AMCA | 316 | 1.3C | 0 |
| 4 | CFl | 316 | | |
| 6 | CTMR | 316 | | |
| 7 | CXR | 316 | | |
| 8 | DECCA | 316 | | |

Each multiple hybridization listed in the table provided similar results. Visual examination of the stained metaphase spreads showed that each labeled probe specifically stained one and only one pair of chromosomes. In addition, each specifically stained pair of chromosomes was distinguishable from the others based upon the color of the light emitted by the stain. Using filter sets #2, #3 (or preferably #13), #5, (or #6), #8, and #9, it was found possible to visualize each of the pairs of target chromosomes from the others.

EXAMPLE 13

Labeling of Chromosome-Specific DNA Probe Precursors with Various Fluorophores

Transaminated of DNA probe precursors prepared as described in Examples 1 and 2 (each respective one of such probe segments having an average length of 300 bp with from 1 to 5% of the total nucleotides thereof aminated at deoxycytidine nucleotides) and each of such probe segments being specific to an individual human chromosome, were each conjugated with one of several amine-reactive fluorophores.

The conjugation reaction conditions varied according to which amino-reactive functionality was present on the fluorophores, the reaction buffer 50 mM (millimolar) sodium borate, pH 9.3. For N-hydroxysuccinimide ester derivatives of fluorophors, the reaction buffer was 200 mM MOPS, pH7.4. 30 to 100 µg DNA/ml for for N-hydroxysuccinimide ester reactions. THe final amine-reactive fluorophore concentrations were 1.2 mM for isothiocyanate derivatives and 2.3 mM for N-hydroxysuccinimide esters. The mM solutions of the amine-reactive fluorophores were prepared by dissolving the fluorophore in a non-reactive solubilizing solvent, such as dimethylformamide (DMF) or dimethylsulfoxide (DMSO). The reaction conditions are summarized in Table XVII below.

EXAMPLE 13

Labeling of Chromosome-Specific DNA Probe Precursors with Various Fluorophores

Transaminated DNA probe segments prepared as described in Examples 1 and 2 (each respective one of such probe segments having an average length of 300 bp with from 1 to 5% of the total nucleotides thereof aminated at deoxycytidine nucleotides) and each of such probe segments being specific to an individual human chromosome, were each conjugated with one of several amine-reactive fluorophores.

The conjugation reaction conditions varied according to which amino-reactive functionality was present on the fluorophores. For isothiocyanate derivatives of fluorophores, the reaction buffer 50 mM sodium borate, pH 9.3. For N-hydroxysuccinimide ester derivatives of fluorophores, the reaction buffer was 200 mM MOPS, pH 7.4. 30 to 100 µg of aminated DNA was dissolved in the reaction buffer and a 20 mM solution of the reactive fluorophore added. The resulting reaction mixture was then mixed continuously overnight, in the dark, at room temperature.

The final DNA concentration in the reaction mixture was 160 µg DNA/ml for isothiocyanate reactions and 100 µg DNA/ml for N-hydroxy-succinimide ester reactions. The final amine-reactive fluorophore concentrations were 1.2 mM for isothiocyanate derivatives and 2.3 mM for N-hydroxysuccinimide esters. The 20 mM solutions of the amine-reactive fluorophores were prepared by dissolving the fluorophore in a non-reactive solubilizing solvent, such as dimethylformamide (DMF) or dimethylsulfoxide (DMSO). The reaction conditions are summarized in Table XVII below.

TABLE XVII

LABELING REACTION CONDITIONS

| FLUOROPHORE | SOLVENT[a] | BUFFER | [FLUOROPHORE][b] (mM) | [DNA] (μg/ml) |
|---|---|---|---|---|
| ISOTHIOCYANATES | | 50 mM Borate, pH 9.3 | 1.2 | 160 |
| EITC | DMF | | | |
| ErITC | DMF | | | |
| N-HYDROXYSUCCINIMIDYL ESTERS | | 0.2 M MOPS, pH 7.4 | 2.3 | 100 |
| HCCA | DMF | | | |
| FCHA | DMSO | | | |
| DMBP | DMF | | | |
| FAP | DMSO | | | |
| OTHER | | | | |
| CBAA | DMSO | 0.1 M NaHCO$_3$, pH 8.4 | 2.3 | 100 |

[a]Fluorophore is dissolved in the specified solvent at a concentration of 20 mM prior to adding the fluorophore stock to the reaction buffer containing the aminated DNA.
[b]Based on 20% amination of dN's, the molar ratio of fluorophore-to-aminated dC is 50 for isothiocyanate reactions and 150 for sulfonic acid chloride and N-hydroxysuccinimide ester reactions.

The labeled probes were purified by ethanol precipitations of the DNA and gel permeation chromatography as follows. Labeled DNA in the reaction mixtures was precipitated by adding 1/10th volume of 2.6 M sodium acetate, pH 5.4, and 2.5×volume of ethanol. The resulting solution was then equilibrated in either a −20° C. freezer overnight or in dry ice for 15 minutes before centrifuging the solution at 7,800×g for 10 minutes. The supernatant was discarded and the labeled DNA pellet dried and resuspended in about 300 μl of water. The DNA solution was then applied to a Sephadex G-25 column (1 cm diam.×28 cm height), which was pre-equilibrated with water, and the purified labeled DNA collected in the column void volume upon elution with water. The labeled DNA was then precipitated a second time with ethanol, either directly from the column solution collected from the column or following volume reduction in a centrifugal evaporator. The precipitated purified labeled DNA was then dissolved in about 300 μl of water and stored frozen at −20° C.

The Cascade Blue acetylazide CBAA was reacted with DNA and purified as described above for N-hydroxysuccinimide esters except that the reaction buffer was 0.1 M NaHCO$_3$, pH 8.4, as recommended by the manufacturer.

The number of labels attached per nucleotide for each probe was determined by the same procedure as employed in the preceding Examples 3–11. Thus, the percentage of nucleotides aminated within a probe was determined prior to fluorophore attachment by the enzymatic digestion/FPLC chromatography procedure described hereinabove. The percentage of nucleotides attached to a fluorophore after labeling was determined from the absorbance spectrum using the absorbance at 260 nm and the absorbance at the long wavelength absorbance maximum of the fluorophore. The ratio of the absorbance at 260 nm to the absorbance at the long wavelength absorbance maximum of the unconjugated dye was multiplied by the long wavelength absorbance of the conjugate and the product subtracted from the absorbance at 260 nm of the conjugate to calculate the absorbance contribution at 260 nm due to DNA. This adjusted absorbance value at 260 nm was divided by an absorbance extinction coefficient of 10,000 $M^{-1}$ $cm^{-1}$ $nucleotide^{-1}$ to obtain the nucleotide concentration of probe in the solution. The long wavelength absorbance maximum of the conjugate was divided by the extinction coefficient of the fluorophore to obtain the fluorophore concentration in conjugate. The percentage of nucleotides attached to fluorophore in the probe was calculated as the ratio of the fluorophore concentration to nucleotide concentration multiplied by 100. There is some present uncertainty in the values of the extinction coefficients of the fluorophore and the DNA, as well as the absorbance ratio of the unconjugated fluorophore, since the extinction coefficients of the fluorophores may be altered by conjugation to the DNA. Also, the calculated labeling percentages are sometimes higher than the percentage amination due to the fact that the probe DNA may not be completely free from unconjugated label. This results either when the label binds to the DNA noncovalently or when the dye forms aggregates which are excluded by the Sephadex G25 columns and precipitate in the ethanol solutions with the DNA. The presence of unconjugated label in the probe preparation does not necessarily mean that a probe will perform poorly in in situ hybridizations.

TABLE XVIII

QUALITATIVE RESULTS OF HYBRIDIZATIONS USING WHOLE CHROMOSOME PAINTING PROBES.

| FLUOROPHORE-PROBE[1] | % AMINATION[2] | % LABELING[3] | [PROBE][4] (ng/10 μl) | VISUAL DESCRIPTION[5] (slide under micropscope-40X) Specificity | Intensity | Filter Set Ref #[6] |
|---|---|---|---|---|---|---|
| HCCA-C4 | 0.90 | 0.48 | 320 | +++ | ++ | 12 |
| HCCA-C4 | 2.9 | 0.90 | 320 | +++ | +++ | 12 |
| EITC-C4 | 0.90 | 0.90 | 320 | +++ | ++++ | 15 |
| EITC-C4 | 2.9 | 1.44 | 320 | ++ | ++++ | 15 |
| ErITC-C4 | 0.90 | 0.87 | 320 | ++ | ++ | 15 |
| ErITC-C4 | 2.9 | 1.02 | 320 | + | ++ | 15 |
| FCHA-C4 | 0.90 | 0.74 | 160 | +++ | +++ | 5, 6, 14 |
| FCHA-C4 | 2.9 | 2.01 | 160 | +++ | ++++ | 5, 6, 14 |
| DMBP-C4 | 0.9 | 0.56 | 320 | ++ | ++/+++ | 5, 6, 14 |
| CBAA-C4 | 2.9 | 1.41 | 316 | ++ | + | 11 |

TABLE XVIII-continued

QUALITATIVE RESULTS OF HYBRIDIZATIONS USING WHOLE CHROMOSOME PAINTING PROBES.

| FLUOROPHORE-PROBE[1] | % AMINATION[2] | % LABELING[3] | [PROBE][4] (ng/10 μl) | VISUAL DESCRIPTION[5] (slide under micropscope-40X) Specificity | Intensity | Filter Set Ref #[6] |
|---|---|---|---|---|---|---|
| FAP-C4 | 1.0 | 0.57 | 160 | +++ | ++++ | 5, 6, 14 |
| FAP-C4 | 3.0 | 0.94 | 160 | ++ | ++++ | 5, 6, 14 |

[1]Labeled probes are indicated as the fluorophore name or abbreviation followed by the number of the chromosome specifically stained by the whole chromosome paint probe (e.g. C4 = chromosome 4).
[2]The percentage of the total nucleotides which contain aliphatic amine linker groups, as determined by enzymatic digestion and FPLC fractionation of nucleosides.
[3]The percentage of the total nucleotides which contain covalently attached fluorophores, as determined by absorbance spectroscopy.
[4]The concentration of labeled probe in the hybridization solution.
[5]Specificity is indicated as follows: (−) = none apparent, (+) = small amount of specificity, (++) = reasonable specificity, (+++) = good specificity, and (++++) = very good specificity. Intensity is indicated as: (−) = not visible, (+) = barely visible, (++) = fairly visible, (+++) = bright, and (++++) = very bright.
[6]See Table V.

In situ hybridizations of whole chromosome painting probes were performed as described in Examples 3–11. Filter sets used to view the fluorescently stained chromosomes are listed in Table V.

Table XVIII presents some qualitative results of in situ hybridizations using the fluorophores described in this example and shown in Table XVII which are in probes that specifically bind to human chromosome #4. These results show that all of these fluorescent labels provide labeled probes which are visually detectable under the microscope and show specificity for staining chromosome #4. The results in Table XVIII also show that the intensity and the specificity of labeled chromosome #4 probe staining is dependent upon the level of probe amination (and therefore labeling). HCCA- and FCHA-labeled probes display similar specificity but increased intensity when the probe is aminated at a level of 3% relative to 1%. EITC-, FAP- and ErITC-labeled probes display similar intensity at both amination levels, but decreased specificity at the higher amination level. For some labels, the optimum amination level is also dependent upon the chromosome library DNA. For example, FAP-labeled chromosome #1 and #7 specific probes performed better with 3% aminated probes than with 1% aminated probes, in contrast to the chromosome #4 specific probe which performed better at 1% amination (results not shown in table). Some variation in the specificity or clarity of green fluorophores stains such as FAP, FCHA and CFL has been observed which variation is greater than that which is observed with, for example, with orange fluorophores such as CTMR.

Quantitative analyses of stained metaphase spreads were performed in order to look more closely at the dependence of probe staining on amination level for some of the labeled probes. The results are presented in Table XIX.

TABLE XIX

QUANTITATIVE PERFORMANCE OF DIFFERENT LABLES AT DIFFERENT LEVELS OF PROBE AMINATION.

| | CHROMOSOME 12 % Amination | | | | CHROMOSOME 4 % Amination | | |
|---|---|---|---|---|---|---|---|
| LABEL | 0.86 | 2.0 | 2.8 | 6.9 | 0.9 | 2.9 | 4.8 |
| HCCA | | | | | | | |
| % Labeling | 0.86 | 0.67 | 1.71 | 2.14 | 0.48 | 0.90 | 1.06 |
| Spec Intensity | 74.9 | 76.6 | 105 | 48.1 | 128 | 150 | 211 |
| Nonspec Intensity | 43.7 | 42.5 | 50.2 | 36.2 | 52.1 | 59.9 | 65.2 |
| Bkg Intensity | 36.7 | 35.2 | 38.3 | 33.9 | 39.3 | 41.6 | 43.0 |
| Gross Spec/Nonspec | 1.72 | 1.80 | 2.09 | 1.33 | 2.46 | 2.50 | 3.24 |
| Net Spec/Nonspec | 5.46 | 5.67 | 5.57 | 6.13 | 6.97 | 5.91 | 7.57 |
| CBAA | | | | | | | |
| % Labeling | | | | | | 1.41 | 2.29 |
| Spec Intensity | | | | | | 301 | 305 |
| Nonspec Intensity | | | | | | 253 | 264 |
| Bkg Intensity | | | | | | 243 | 252 |
| Gross Spec/Nonspec | | | | | | 1.19 | 1.16 |
| Net Spec/Nonspec | | | | | | 6.13 | 4.36 |

TABLE XIX-continued

QUANTITATIVE PERFORMANCE OF DIFFERENT LABLES AT DIFFERENT LEVELS OF PROBE AMINATION.

| | CHROMOSOME 12 % Amination | | | | CHROMOSOME 4 % Amination | | |
|---|---|---|---|---|---|---|---|
| LABEL | 0.86 | 2.0 | 2.8 | 6.9 | 0.9 | 2.9 | 4.8 |
| ErITC | | | | | | | |
| % Labeling | | | | | 0.87 | 1.02 | |
| Spec Intensity | | | | | 44.4 | 41.9 | |
| Nonspec Intensity | | | | | 33.5 | 31.8 | |
| Bkg Intensity | | | | | 26.8 | 25.6 | |
| Gross Spec/Nonspec | | | | | 1.32 | 1.32 | |
| Net Spec/Nonspec | | | | | 2.61 | 2.65 | |
| EITC | | | | | | | |
| % Labeling | 0.57 | 0.45 | 0.54 | 0.88 | 0.90 | 1.44 | 1.26 |
| Spec Intensity | 122 | 81.6 | 64.9 | 182 | 227 | 436 | 135 |
| Nonspec Intensity | 73.7 | 54.7 | 48.8 | 128 | 80.6 | 178 | 99.6 |
| Bkg Intensity | 56.7 | 47.6 | 43.9 | 84.6 | 52.4 | 99.1 | 67.3 |
| Gross Spec/Nonspec | 1.66 | 1.49 | 1.33 | 1.42 | 2.81 | 2.45 | 1.36 |
| Net Spec/Nonspec | 3.85 | 4.81 | 4.30 | 2.24 | 6.17 | 3.46 | 2.11 |
| FCHA | | | | | | | |
| % Labeling | 0.66 | 1.30 | 1.75 | 3.14 | 0.74 | 2.01 | 3.63 |
| Spec Intensity | 170 | 307 | 345 | 382 | 269 | 760 | 437 |
| Nonspec Intensity | 95.3 | 156 | 113 | 248 | 128 | 208 | 152 |
| Bkg Intensity | 57.8 | 7.45 | 62.1 | 153 | 70.4 | 108 | 94.6 |
| Gross Spec/Nonspec | 1.78 | 1.97 | 3.05 | 1.54 | 2.09 | 3.66 | 2.87 |
| Net Spec/Nonspec | 2.99 | 2.85 | 5.55 | 2.41 | 3.42 | 6.54 | 5.95 |
| DMBP | | | | | | | |
| % Labeling | 0.38 | 0.71 | 1.01 | 0.56 | 0.56 | 1.51 | 2.14 |
| Spec Intensity | 31.2 | 48.2 | 48.3 | 60.7 | 39.2 | 87.1 | 101 |
| Nonspec Intensity | 23.8 | 26.7 | 27.6 | 32.7 | 27.2 | 35.9 | 41.3 |
| Bkg Intensity | 21.8 | 22.3 | 23.3 | 25.6 | 24.1 | 26.6 | 29.8 |
| Gross Spec/Nonspec | 1.31 | 1.80 | 1.75 | 1.86 | 1.44 | 2.42 | 2.45 |
| Net Spec/Nonspec | 4.84 | 5.88 | 5.70 | 4.94 | 4.91 | 6.48 | 6.24 |

Analyses were performed by first recording a digital image of a fluorescently-stained metaphase spread using a cooled CCD camera (Photometrics, Tucson, Ariz., Series 200 camera) interfaced to a Macintosh II fx computer. Image processing software (IP Labs, Signal Analytics, Vienna, Va.) was used to separately determine the average image pixel intensity of the specifically-stained chromosomes (Spec Intensity), the remaining chromosomes (Nonspec Intensity), and the non-chromosome region (Bkg Intensity). Specificity is considered to be the ratio of the specifically stained chromosome intensity-to-the nonspecifically-stained chromosome intensity, either before (Gross Spec/Nonspec) or after (Net Spec/Nonspec) subtraction of the background intensity.

The intensities and specificities (intensity ratios) listed in Table XIX show several significant trends. In general, the specific stain intensities increase with increasing probe amination level, and hence percent labeling. Often the increase in intensity with amination level reaches a maximum value and decreases with further increase in amination level. The specificities also show a similar behavior. Ideally, the intensity and specificity would be maximal at the same amination level and this would present the optimal amination level for that particular probe DNA and label. This is not always the case, however, and the optimal amination level must be selected as a trade off between intensity and specificity. Another factor that affects these values is probe concentration. At lower concentrations, the specificity usually improves while the intensity decreases. A probe which provides a high intensity stain and a low specificity can benefit by lowering the probe concentration to improve the specificity. If the intensity of the probe staining is already low, then lowering the probe concentration may improve the specificity, but reduces the staining intensity to an unacceptable level.

The numbers listed in Table XIX reflect only average intensities within a metaphase region. Variations of intensity along a chromosome or outside of the chromosomes are lost in these calculations. Therefore, specificity can actually be lower than indicated by the averages. For example, a labeled-chromosome #6 probe might stain small regions of chromosomes other than #6 as intensely as it stains chromosome #6. This could be a commercially unacceptable specificity, however, the average intensities of the non-specifically stained chromosomes would still be low due to averaging the bright "spots" over the whole chromosomes, and the lack of specificity would be missed. Therefore, visual observations of background and chromosome staining must be considered with the digital information. Considering the digital and visual information, the optimal amination levels for the various probes are now believed to be about 3% for HCCA, CBAA, FCHA, and DMBP, and about 1% for EITC and ErITC based on available data. These are very general numbers since some chromosome-to-chromosome variation is observed in the optimal amination levels and these analyses are based upon only the laboratory work described here.

EXAMPLE 14

Direct Label Probe Composition Specifically Complementary to the Centromere Region of Human Chromosome #12

A cloned DNA sequence known to be specifically complementary to the centromere region of human chromosome #12 was prepared by the procedure described in Bittner et al. U.S. Pat. Ser. No. 07/762,912 published as PCT Patent Application WO 93/0246, on Apr. 1, 1993, filed on even date herewith, (identified as purified plasmid DNA cloned sequence #1-1, and having a 3.5 k bp insert, and known to contain DNA repeated sequences). This sequence was disrupted into small fragments of approximately 300 base pairs by sonication using a Branson Sonifier 450 (Danbury, Conn.). DNA from the plasmid preparation was sonicated in 2 mls of water at a concentration of 500 µg/ml. The solution was contained in a 5 ml polypropylene tube which was immersed in a dry ice/ethanol bath to prevent boiling during sonication. The microtip of the sonication device was immersed in this solution until the tip was 2–5 mm from the bottom of the tube. Sonication was carried out at an output power of 25–30 watts, discontinuously, with an 80% duty cycle (on 80% of the time, off 20% of the time), for a period of 5–7 minutes. Following sonication, the DNA was precipitated by the addition of 0.2 ml of 3M sodium acetate (pH 5.5) and 4.5 mls of ethanol. The precipitate was recovered by centrifugation for 5 minutes at 8,000×g and vacuum dried.

To prepare bisulfite buffer, 1.7 ml of concentrated HCl was slowly added to 1 ml of deionized $H_2O$ on ice. 1 ml fresh ethylene diamine (Sigma Cat. #E-4379) was then slowly added on ice. After dissolution of the ethylene diamine, the solution was warmed to room temperature and 0.475 g sodium metabisulfite (Aldrich Cat. #25, 555-6) was added. Concentrated HCl was then slowly added to the bisulfite mixture until the pH reached 7.0 and the volume of the solution was adjusted to 5.0 ml.

To transaminate probe DNA, 1 mg of sonicated DNA was resuspended in 500 µl of water. The DNA was denatured by boiling at 100° C. for 5 minutes then quickly chilled in an ice water bath. The transamination reaction was initiated by the addition of 4.5 ml of bisulfite buffer. Reaction in bisulfite buffer was allowed to proceed for 2 days at 37° C. The DNA solution was desalted by routine dialysis against 5–10 mM sodium borate buffer (pH 8.0). After dialysis, 0.6 ml of 3M sodium acetate (pH 5.5) was added. The aminated DNA was precipitated with 2 volumes of ethanol and recovered after centrifugation at 8,000×g for 10 minutes. The pellets were vacuum dried and resuspended in 1 ml of water.

The extent of transamination of deoxycytidine was determined by enzymatic digestion of the aminated DNA followed by separation of the resulting nucleotides on an FPLC chromatography system as described in Example 2. This analysis indicated that 3.4% of total nucleotides or 13.6% of deoxycytidines were transaminated.

Forty micrograms of aminated DNA sequence 1-1 derived from human chromosome #12 as described in the afore referenced Bittner, et al. application Ser. No. 07/762,912 filed on even date herewith, published as PCT Patent Application WO 93/0246, on Apr. 1, 1993, was dried into a 2 ml tube then resuspended in 362 µl 0.20 M MOPS (3-[N-Morpholino]propanesulfonic acid), pH 7.4. The fluorescent compound 5- (and-6) carboxytetramethylrhodamine (CTMR), succinimidyl ester was dissolved in dimethylformamide to 30 mm. A 150-fold molar excess of the fluorophore relative to the intermediate transaminated nucleotides (assuming 5% of the total nucleotides are transaminated) was added to the DNA, in this case 37.9 µl of 30 mM CTMR. This labeling reaction proceeded in darkness at room temperature with the tube rotating overnight.

The purification of the labeled probe away from the excess fluorophore was a three step procedure. The first step was an ethanol precipitation. Any remaining ethanol was evaporated from the precipitated pellet, then the probe was resuspended in 300 µl water. This solution was passed over a Sephadex G-25 column 28 cm high and 1 cm diameter. The desired fraction (the column void volume) was eluted with water and dried to reduce the total volume. A second ethanol precipitation completed the purification and the dried pellet was resuspended in 300 µl water. An absorbance spectrum of the labeled probe showed 3.3% of the total nucleotides were labeled.

EXAMPLE 15

Detection of the Centromere Region of Chromosome #12 by In Situ Hybridization The probe composition of the preceding Example 14 was used to identify (detect) the centromere region of human chromosome #12 as follows:

The target DNA consisted of cultured normal white blood cells that were treated to arrest the cells in metaphase. These cells were dropped onto a microscope slide from a distance of about 2 to 3 feet to break open the nuclei and expose the chromosomes. Unbroken or interphase cells were also present on the slide surface. Before hybridizing, the slide was placed in a denaturing solution consisting of 70% formamide/0.3 MNaCl/30 mM sodium citrate, pH 7.0, for 2 minutes at 70° C. The slide was then dehydrated by passage through 70%, 85%, and 100% ethanol baths (2 minutes each). The slide was then warmed to approximately 40° C.

The hybridization mix that was placed on each slide was always 55% formamide/10% dextran sulfate/0.15 M NaCl/ 15 mM sodium citrate, pH 7.0. The concentrations of probe added to the basic hybridization mix varied to determine the optimal concentration needed to obtain acceptable signal intensity and specificity. The reaction mixture also contained 4.5 µg of sonicated human placental DNA added as carrier and blocking DNA. In addition to the unlabeled human placental DNA, approximately 96 ng of fluorescein labeled, sonicated human placental DNA was added as a genomic counterstain. The preparation of such genomic counterstain is taught in copending Morrison et al. U.S. Ser. No. 07/762, 928 filed on even date herewith, published as PCT Patent Application WO 93/0245 on Apr. 1, 1993. Ten µl of the completed hybridization mixture was denatured by heating at 70° C. for from 5 to 15 minutes and then incubated at 37° C. for 5 minutes. The mix was applied directly to the slide, covered with a glass coverslip whose edges were sealed with rubber cement, and allowed to hybridize overnight at 42° C. in a humidified chamber.

The next day the unbound probe was removed by washing the slide (three times, each for 15 minutes at 45° C.) in 0.3 MNaCl/30 mM sodium citrate 50% formamide v/v, pH 7.0. A single wash (15. minutes at 45° C.) in 0.3 M NaCl/30 mM sodium citrate (2×SCC, pH 7.0), followed. The final wash (15 minutes at 45° C.) was in 0.1 M sodium phosphate/0.1% NP40 detergent (PN buffer). Finally, the slide was washed twice in PN buffer (2 minutes at room temperature), and air dried. Ten microliters of antifade was placed over the target cells and a coverslip was placed over that. The slides were viewed with a fluorescence microscope.

Results are tabulated in Table XX below:

TABLE XX

Qualitative Results

| Hybridization Conditions | | Visual Description | |
| --- | --- | --- | --- |
| CTMR Probe (3) | Concentration (ng/10 µl) | (1) Intensity | (2) Specificity |
| #1-1 | 33 | ++++ | ++++ |
| | 100 | ++++ | ++++ |

(1) Intensity: (−) not visible, (+) barely visible, (++) fairly visible, (+++) bright, (++++) very bright, (NE) cannot be evaluated
(2) specificity: (−) none apparent, (+) low specificity, (++) reasonable specificity, (++++) good specificity, (NE) cannot be evaluated
(3) Blocking DNA present (4.5 µg human placental DNA/10 µl)

On the basis of the above results it is concluded that direct attachment of the flurophore to the alphoid DNA probe of Example 14 produces a probe composition which can readily be utilized for in situ hybridization analysis of specific centromeres.

EXAMPLE 16

Direct Label Probe Composition Specifically Complementary to the Centromere Region of Human Chromosome #8

A cloned DNA sequence known to be specifically complementary to the centromere region of human chromosome #8 was prepared by the procedure described in afore described Bittner et al. U.S. Ser. No. 07/762,912 filed on even date herewith published as PCT Patent Application WO 93/0246, on Apr. 1, 1993 (identified as purified plasmid DNA cloned sequence 10-4).

The DNA sequence from plasmid 10-4 was prepared by fermentation. Bacteria containing the plasmid 10-4 were streaked onto a YT agar plate containing 200 µg/ml of ampicillin. A single colony from this plate was transferred into 2 ml of 2 YT broth and allowed to grow overnight at 30° C. with agitation. This bacterial suspension served as the seed stock for the fermentation process described in such Bittner et al. U.S. Ser. No. 07/762,912, published as PCT Patent Application WO 93/0246, on Apr. 1, 1993 and the fermented culture and extraction of the DNA sequence were as described therein. Fermentation yielded a cell mass of 204 grams. Extraction of 122 grams of this pellet yielded 60 milligrams of plasmid DNA. 1 milligram of the resulting plasmid 10-4 DNA sequence was sonicated as described in such Bittner et al. U.S. Ser. No. 07/762,912, published as PCT Patent Application WO 93/0246, on Apr. 1, 1993. One milligram of this sonicated DNA was resuspended in 1 ml of distilled water. The DNA was denatured by boiling for 5 minutes and quickly cooling on ice.

9 mls of bisulfite buffer were added and a transamination reaction as described in Example 14 was allowed to proceed for 2 days at 37° C. DNA product which resulted was desalted by routine dialysis against 10 mM sodium borate (pH 8.0). This resulting DNA was precipitated by the addition of 0.1 volume of 3 M sodium acetate (pH 5.5) and 2.5 volumes of ethanol, and the precipitated DNA was resuspended in water at a concentration of 1 mg/ml. Forty micrograms of the resulting aminated DNA sequence 10-4 to the centromere of chromosome #8 was dried into a 2 ml tube and then resuspended in 362 µl 0.20 M MOPS (3-[N-Morpholino]propanesulfonic acid), pH 7.4. The fluorescent compound 5- (and-6) carboxytetramethylrhodamine (CTMR), succinimidyl ester was dissolved in dimethylformamide to 30 mM. A 150-fold molar excess of this fluorophore was added to the aminated DNA, in this case 37.9 µl of 30 mM CTMR. This labeling reaction proceeded in darkness at room temperature with the tube rotating overnight.

The purification of the labeled probe away from the excess fluorophore was a subsequent three step procedure. The first step was an ethanol precipitation. Any remaining ethanol was evaporated from the precipitated pellet, then the probe was resuspended in 300 µl water. This solution was passed over a Sephadex G-25 column 28 cm high and 1 cm in diameter. The desired fraction (the column void volume) was eluted with water and dried to reduce the total volume. A second ethanol precipitation completed the purification and the dried pellet was resuspended in 300 µl water. An absorbance spectrum of the resulting direct label probe composition showed 3.1% of the total nucleotides were labeled.

EXAMPLE 17

Detection of the Centromere Region of Chromosome #8 by In Situ Hybridization

The probe composition of the preceding Example 16 was used to identify (detect) the centromere region of human Chromosome #8 as follows:

16 ng of the direct label probe composition of Example 16 above was dried into a 0.5 ml tube with a tight-fitting cap. The probe was resuspended in 10 µl of 55% formamide/10% dextran sulfate/0.15M NaCl/15 mM sodium citrate, pH 7.0, with 4.5 µg sonicated human placental DNA being added as blocker. This hybridization mixture was denatured by placing the tube in a 70° C. water bath for 5 minutes.

A target slide which was prepared as described in Example 15 above was denatured for 3 minutes in a 70° C. solution of 70% formamide/2×SSC and then dehydrated by passing successively through 70%, 85%, and 100% ethanol baths (2 minutes each). A drop of the thus previously de-natured hybridization mixture was pipetted onto the slide and the drop was covered with a coverslip. The coverslip was sealed onto the slide with rubber cement. The hybridization was allowed to proceed overnight in a dark, humidified 37° C. chamber.

The next day the residual unbound probe was removed by washing the slide (three times, each for 15 minutes at 45° C.) in 50% formamide/0.3MNaCl/30 mM sodium citrate, pH 7.0. A single wash (15 minutes at 45° C.) in 0.3M NaCl/30 mM sodium citrate (2×SSC, pH 7.0), followed. The slide was next washed in 0.1 M sodium phosphate/0.1% NP40 detergent (PN buffer) (15 minutes at 45° C.). Finally, the slide was washed twice in PN buffer (2 minutes at room temperature), and air dried. 7.5 µl of 1 µg/ml DAPI in an antifade solution was placed over the target cells and a coverslip was placed over that.

The results obtained were tabulated as follows in Table XXI:

The technique and advantages of employing a chaotrope in the transamination are taught in the aforereferenced Bittner et al. U.S. Ser. No. 07/762,912 published as PCT Patent Application WO 93/0246, on Apr. 1, 1993, filed on even date herewith.

TABLE XXI

Results of In Situ Hybridization with Fluorophore Direct Label Probe

| Hybridization Conditions | | Visual Description | |
| --- | --- | --- | --- |
| CTMR (3) Probe | Concentration (ng/10 µl) | (1) Intensity | (2) Specificity |
| #10-4 (9 kbp insert) | 16 | ++++ | ++++ |

Table XXI footnotes:
(1) Intensity: (−) not visible, (+) barely visible, (++) fairly visible, (+++) bright, (++++) very bright, (NE) cannot be evaluated
(2) Specificity: (−) none apparent, (+) low specificity, (++) reasonable specificity, (++++) good specificity, (NE) cannot be evaluated
(3) * blocking DNA present (4.5 µg human placental DNA/10 µl)
Based on the above indicated results, it was concluded that the so produced direct label probe composition is well suited for use in in situ hybridization enumerations of specific chromosome centromeres using fluoroscopic analysis. Other and further embodiments will be apparent in the art from the preceding description and examples. No unreasonable limitations or the like to be drawn therefrom.

What is claimed is:

1. A method of simultaneous detection of at least two preselected target chromosomes or target chromosome regions by in situ hybridization using multiple direct label DNA probes comprising:
   (a) providing a plurality of at least two direct label DNA probes compositions, wherein each of the direct label DNA probe compositions:
      (i) comprise direct label DNA segments which are complementary to a single target chromosome or target chromosome region and have fluorescent labels directly linked to the DNA segments, and
      (ii) is detectable by use of a different fluorescent color, each color being detectable in the presence of other direct label probe compositions;
   (b) contacting the plurality of direct label DNA probe compositions under hybridizing conditions in in situ hybridization with a plurality of target chromosomes or target chromosome regions contained in a target specimen; and
   (c) detecting the target chromosomes or target chromosome regions by identification of two or more fluorescent colors using a digital image of the target specimen.

2. The method of claim 1 which further comprises adding an excess of blocking DNA segments to the multiple probe composition.

3. The method of claim 1 wherein the direct label DNA segments comprise fluorescent labels covalently linked to the direct label DNA segments via transaminated cytosine sites.

4. The method of claim 1 wherein the target specimen comprises at least one human interphase cell.

5. The method of claim 1 wherein the target chromosomes or target regions of a chromosome are contained in human amniotic cells.

6. The method of claim 1 wherein the target chromosomes or target regions of a chromosome are extracted from tissue.

7. The method of claim 1 wherein said fluorescent labels are each derivatives of a compound selected from the group consisting of 7-amino-4-methylcoumarin-3-acetic acid, succinimidyl ester; Texas Red sulfonyl chloride; 5- (and 6-)-carboxy-X-rhodamine, succinimidyl ester; Lissamine rhodamine B sulfonyl chloride; 5- (and 6-)-carboxyfluorescein, succinimidyl ester; fluorescein-5-isothiocyanate; 7-diethylaminocoumarin-3-carboxylic acid, succinimidyl ester; tetramethylrhodamine 5- (and 6-)isothiocyanate; 5- (and 6-)carboxytetramethylrhodamine, succinimidyl ester; 7-hydroxycoumarin-3-carboxylic acid, succinimidyl ester; and 6-hexanoic acid, succinimidyl ester.

8. The method of claim 1 wherein at least four preselected target chromosome regions are detected.

9. The method of claim 1 wherein at least five preselected target chromosome regions are detected.

10. The method of claim 1 wherein a digital image is made using a CCD camera.

11. The method of claim 1 further comprising determining pixel intensity of the fluorescent colors.

12. The method of claim 11 wherein the target specimen is human tissue.

13. The method of claim 11 wherein at least four preselected target chromosome regions are detected.

14. The method of claim 11 wherein the direct label DNA segments comprise fluorescent labels covalently linked to the direct label DNA segments via transaminated cytosine sites.

15. The process of claim 1 wherein:
   (a) said specimen is comprised of cytological material that is distributed as an adhering layer upon one surface of a slide;
   (b) said contacting is carried out by applying an aqueous solution of said probe composition to said specimen using hybridizing conditions;
   (c) said separating is carried out by washing said resulting specimen with an aqueous liquid; and
   (d) said examining is carried out with a fluorescence microscope.

16. The process of claim 1 wherein:
   (a) said specimen is comprised of an aqueous suspension containing said selected chromosome or selected region;
   (b) said contacting is carried out by dissolving said probe composition in said suspension;
   (c) said separating is carried out by centrifuging; and
   (d) said examining is carried out with a flow cytometer.

* * * * *